United States Patent
Beigelman et al.

(10) Patent No.: US 11,939,581 B2
(45) Date of Patent: Mar. 26, 2024

(54) METHODS AND COMPOSITIONS FOR TARGETING PD-L1

(71) Applicant: ALIGOS THERAPEUTICS, INC., South San Francisco, CA (US)

(72) Inventors: Leonid Beigelman, San Francisco, CA (US); Megan Elizabeth Fitzgerald, San Francisco, CA (US); Saul Martinez Montero, San Francisco, CA (US); Aneerban Bhattacharya, San Mateo, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 4 days.

(21) Appl. No.: 17/249,337

(22) Filed: Feb. 26, 2021

(65) Prior Publication Data

US 2021/0277403 A1    Sep. 9, 2021

Related U.S. Application Data

(60) Provisional application No. 62/983,114, filed on Feb. 28, 2020.

(51) Int. Cl.

| | | |
|---|---|---|
| *C12N 15/113* | (2010.01) | |
| *A61K 31/7105* | (2006.01) | |
| *A61K 45/06* | (2006.01) | |
| *A61P 31/20* | (2006.01) | |
| *A61P 35/00* | (2006.01) | |

(52) U.S. Cl.
CPC ...... *C12N 15/1138* (2013.01); *A61K 31/7105* (2013.01); *A61K 45/06* (2013.01); *A61P 31/20* (2018.01); *A61P 35/00* (2018.01); *C12N 2310/14* (2013.01); *C12N 2310/315* (2013.01); *C12N 2310/321* (2013.01)

(58) Field of Classification Search
CPC ............ C12N 15/1138; C12N 2310/14; C12N 2310/315; C12N 2310/321; A61P 31/20
See application file for complete search history.

(56) References Cited

U.S. PATENT DOCUMENTS

| | | | |
|---|---|---|---|
| 8,507,663 B2 | 8/2013 | DeFougerolles et al. | |
| 2008/0113351 A1* | 5/2008 | Naito | A61P 5/26 536/23.1 |
| 2011/0251259 A1* | 10/2011 | DeFougerolles | A61K 31/713 435/325 |

FOREIGN PATENT DOCUMENTS

| | | | |
|---|---|---|---|
| WO | WO 2005/007855 A2 | 1/2005 | |
| WO | WO 2017/040078 A1 | 3/2017 | |
| WO | WO-2017100587 A1 * | 6/2017 | ......... A61K 31/7088 |

OTHER PUBLICATIONS

Gevensleben, H. et al., 'The Immune Checkpoint Regulator PD-L1 is Highly Expressed in Aggressive Primary Prostate Cancer'. Clinical Cancer Research. Apr. 2016, vol. 22, issue 8 siRNA transfection for transient knockdown of PD-L1.
S26548 siRNA [retrieved from internet on Apr. 13, 2021]<URL: https://www.thermofisher.com/order/genome-database/details/sirna/s26548#assay-details-section> published on Sep. 26, 2015.
Setten, R. et al., 'The current state and future directions of RNAi-based therapeutics'. Nature Reviews Drug Discovery. Mar. 2019, vol. 18, pp. 421-446.
TranslationBlocker Human PD-L1 / CD274 siRNA [retrieved from internet on Apr. 22, 2021]<URL: https://enquirebio.com/rnai/qx7-human-pd-11-cd274-sirna-translation-blocker-duplex> published on Jan. 16, 2018.
Weng, Y. et al., 'RNAi therapeutic and its innovative biotechnological evolution'. Biotechnology Advances. Apr. 2019, vol. 37, pp. 801-825.
Wu, Y. et al., 'Silencing PD-1 and PD-L1 with nanoparticle-delivered small interfering RNA increases cytotoxicity of tumor-infiltrating lymphocytes'. Nanomedicine. Mar. 2019, vol. 14, pp. 955-967 Knockdown of PD-1 in TILs & PD-L1 in MCF-7 with siRNAs delivered by LCP NPs and Chemicals.
International Search Report and Written Opinion issued in application No. PCT/US2021/019628, dated May 3, 2021.

* cited by examiner

*Primary Examiner* — Brian Whiteman
(74) *Attorney, Agent, or Firm* — KNOBBE MARTENS OLSON & BEAR LLP

(57) ABSTRACT

The present disclosure relates to small interfering RNA (siRNA) molecules directed to mRNA transcripts of CD274 to cause downregulation of programmed death-ligand 1 (PD-L1) expression in humans. The siRNA can be constructed of unmodified nucleotides or modified nucleotides that exhibit modified sugars, nucleobases, linkages, or covalently bound targeting moieties. Also disclosed herein are pharmaceutical compositions of siRNAs and uses of or methods of using the siRNAs for the treatment of PD-L1 related diseases including but not limited to liver diseases, cancer, hepatocellular carcinoma, viral diseases, or hepatitis B.

18 Claims, 2 Drawing Sheets
Specification includes a Sequence Listing.

SEQUENCE LISTING

```
<160> NUMBER OF SEQ ID NOS: 380

<210> SEQ ID NO 1
<211> LENGTH: 3634
<212> TYPE: DNA
<213> ORGANISM: Artificial Sequence
<220> FEATURE:
<223> OTHER INFORMATION: Human CD274

<400> SEQUENCE: 1
agttctgcgc agcttcccga ggctccgcac cagccgcgct tctgtccgcc tgcagggcat      60
tccagaaaga tgaggatatt tgctgtcttt atattcatga cctactggca tttgctgaac     120
gcatttactg tcacggttcc caaggaccta tatgtggtag agtatggtag caatatgaca     180
attgaatgca aattcccagt agaaaaacaa ttagacctgg ctgcactaat tgtctattgg     240
gaaatggagg ataagaacat tattcaattt gtgcatggag aggaagacct gaaggttcag     300
catagtagct acagacagag ggcccggctg ttgaaggacc agctctccct gggaaatgct     360
gcacttcaga tcacagatgt gaaattgcag gatgcagggg tgtaccgctg catgatcagc     420
tatggtggtg ccgactacaa gcgaattact gtgaaagtca atgccccata caacaaaatc     480
```

-continued

```
aaccaaagaa ttttggttgt ggatccagtc acctctgaac atgaactgac atgtcaggct    540
gagggctacc ccaaggccga agtcatctgg acaagcagtg accatcaagt cctgagtggt    600
aagaccacca ccaccaattc caagagagag gagaagcttt tcaatgtgac cagcacactg    660
agaatcaaca caacaactaa tgagattttc tactgcactt ttaggagatt agatcctgag    720
gaaaaccata cagctgaatt ggtcatccca gaactacctc tggcacatcc tccaaatgaa    780
aggactcact tggtaattct gggagccatc ttattatgcc ttggtgtagc actgacattc    840
atcttccgtt taagaaaagg gagaatgatg gatgtgaaaa aatgtggcat ccaagataca    900
aactcaaaga agcaaagtga tacacatttg gaggagacgt aatccagcat tggaacttct    960
gatcttcaag cagggattct caacctgtgg tttaggggtt catcggggct gagcgtgaca   1020
agaggaagga atgggcccgt gggatgcagg caatgtggga cttaaaaggc caagcactg   1080 aaaatggaac ctggcgaaag cagaggagga gaatgaagaa agatggagtc aaacagggag   1140
cctggaggga gaccttgata ctttcaaatg cctgagggc tcatcgacgc ctgtgacagg    1200
gagaaaggat acttctgaac aaggagcctc caagcaaatc atccattgct catcctagga   1260
agacgggttg agaatcccta atttgagggt cagttcctgc agaagtgccc tttgcctcca   1320
ctcaatgcct caatttgttt tctgcatgac tgagagtctc agtgttggaa cgggacagta   1380
tttatgtatg agttttcct atttattttg agtctgtgag gtcttcttgt catgtgagtg    1440
tggttgtgaa tgatttcttt tgaagatata ttgtagtaga tgttacaatt ttgtcgccaa    1500
actaaacttg ctgcttaatg atttgctcac atctagtaaa acatggagta tttgtaaggt   1560
gcttggtctc ctctataact acaagtatac attggaagca taaagatcaa accgttggtt   1620
gcataggatg tcacctttat ttaacccatt aatactctgg ttgacctaat cttattctca   1680
gacctcaagt gtctgtgcag tatctgttcc atttaaatat cagctttaca attatgtggt   1740
agcctacaca cataatctca tttcatcgct gtaaccaccc tgttgtgata accactatta   1800
ttttacccat cgtacagctg aggaagcaaa cagattaagt aacttgccca aaccagtaaa   1860
tagcagacct cagactgcca cccactgtcc ttttataata caatttacag ctatatttta   1920
ctttaagcaa ttcttttatt caaaaaccat ttattaagtg cccttgcaat atcaatcgct   1980
gtgccaggca ttgaatctac agatgtgagc aagacaaagt acctgtcctc aaggagctca   2040
tagtataatg aggagattaa caagaaaatg tattattaca atttagtcca gtgtcatagc   2100
ataaggatga tgcgagggga aaacccgagc agtgttgcca agaggaggaa ataggccaat   2160
gtggtctggg acggttggat atacttaaac atcttaataa tcagagtaat ttcatttac    2220 aaagagaggt cggtacttaa aataaccctg aaaaataaca ctggaattcc ttttctagca   2280 ttatattat tcctgatttg cctttgccat ataatctaat gcttgttat atagtgtctg    2340 gtattgttta acagttctgt cttttctatt taaatgccac taaattttaa attcatacct   2400
ttccatgatt caaaattcaa aagatcccat gggagatgt tggaaaatct ccacttcatc    2460
ctccaagcca ttcaagtttc cttttccagaa gcaactgcta ctgcctttca ttcatatgtt   2520
cttctaaaga tagtctacat ttggaaatgt atgttaaaag cacgtatttt taaaattttt   2580
ttcctaaata gtaacacatt gtatgtctgc tgtgtacttt gctattttta tttatttag    2640 tgtttcttat atagcagatg gaatgaattt gaagttccca gggctgagga tccatgcctt   2700 cttttgtttct aagttatctt tcccatagct tttcattatc tttcatatga tccagtatat   2760
gttaaatatg tcctacatat acatttagac aaccaccatt tgttaagtat ttgctctagg   2820
```

```
acagagtttg gatttgttta tgtttgctca aaaggagacc catgggctct ccagggtgca      2880
ctgagtcaat ctagtcctaa aaagcaatct tattattaac tctgtatgac agaatcatgt      2940 ctggaactt tgttttctgc tttctgtcaa gtataaactt cactttgatg ctgtacttgc       3000
aaaatcacat tttcttctg gaaattccgg cagtgtacct tgactgctag ctaccctgtg       3060
ccagaaaagc tcattcgtt gtgcttgaac ccttgaatgc caccagctgt catcactaca       3120
cagccctcct aagaggcttc ctggaggttt cgagattcag atgccctggg agatcccaga      3180 gtttccttc cctcttggcc atattctggt gtcaatgaca aggagtacct tggctttgcc       3240
acatgtcaag gctgaagaaa cagtgtctcc aacagagctc cttgtgttat ctgtttgtac      3300
atgtgcattt gtacagtaat tggtgtgaca gtgttctttg tgtgaattac aggcaagaat      3360
tgtggctgag caaggcacat agtctactca gtctattcct aagtcctaac tcctccttgt      3420
ggtgttggat ttgtaaggca ctttatccct tttgtctcat gtttcatcgt aaatggcata      3480
ggcagagatg atacctaatt ctgcatttga ttgtcacttt ttgtacctgc attaatttaa      3540
taaaatattc ttatttattt tgttacttgg tacaccagca tgtccatttt cttgtttatt      3600
ttgtgtttaa taaaatgttc agtttaacat ccca                                  3634

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 2
acagcaaata tcctcatc                                                    18

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 3
gacagcaaat atcctcat                                                    18

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 4
agacagcaaa tatcctca                                                    18

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 5
aagacagcaa atatcctc                                                    18

<210> SEQ ID NO 6
<211> LENGTH: 18
```

```
<212> TYPE: DNA
<213> ORGANISM: Artificial Sequence
<220> FEATURE:
<223> OTHER INFORMATION: Synthetic Oligonucleotide

<400> SEQUENCE: 6
aaagacagca aatatcct                                                   18

<210> SEQ ID NO 7
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 7
taaagacagc aaatatcc                                                   18

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
ataaagacag caaatatc                                                   18

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
tataaagaca gcaaatat                                                   18

<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 10
atataaagac agcaaata                                                   18

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
aatataaaga cagcaaat                                                   18

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
```
agactcaaaa taaatagg                                                    18

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
cagactcaaa ataaatag                                                    18

<210> SEQ ID NO 14
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 14
acagactcaa aataaata                                                    18

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
cacagactca aaataaat                                                    18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
tcacagactc aaaataaa                                                    18

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
ctcacagact caaaataa                                                    18

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18
cctcacagac tcaaaata                                                    18

<210> SEQ ID NO 19
<211> LENGTH: 18
<212> TYPE: DNA
<213> ORGANISM: Artificial Sequence

```
<220> FEATURE:
<223> OTHER INFORMATION: Synthetic Oligonucleotide

<400> SEQUENCE: 19
acctcacaga ctcaaaat                                                 18

<210> SEQ ID NO 20
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 20
gacctcacag actcaaaa                                                 18

<210> SEQ ID NO 21
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 21
agacctcaca gactcaaa                                                 18

<210> SEQ ID NO 22
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 22
ataacttaga aacaaaga                                                 18

<210> SEQ ID NO 23
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 23
gataacttag aaacaaag                                                 18

<210> SEQ ID NO 24
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 24
agataactta gaaacaaa                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 25
cttcaggtct tcctctcc                                                 18
```

<210> SEQ ID NO 26
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 26
ggtagctagc agtcaagg                                                 18

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
gggtagctag cagtcaag                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 28
agggtagcta gcagtcaa                                                 18

<210> SEQ ID NO 29
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 29
cagggtagct agcagtca                                                 18

<210> SEQ ID NO 30
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 30
ttcagccttg acatgtgg                                                 18

<210> SEQ ID NO 31
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 31
cttcagcctt gacatgtg                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide

```
<400> SEQUENCE: 32
tcttcagcct tgacatgt                                              18

<210> SEQ ID NO 33
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 33
ttcttcagcc ttgacatg                                              18

<210> SEQ ID NO 34
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 34
tttcttcagc cttgacat                                              18

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 35
gaagtgcagc atttccca                                              18

<210> SEQ ID NO 36
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 36
tgaagtgcag catttccc                                              18

<210> SEQ ID NO 37
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 37
ctgaagtgca gcatttcc                                              18

<210> SEQ ID NO 38
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 38
tttattaaat taatgcag                                              18

<210> SEQ ID NO 39
```

```
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 39
ttttattaaa ttaatgca                                                   18

<210> SEQ ID NO 40
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 40
attttattaa attaatgc                                                   18

<210> SEQ ID NO 41
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 41
tctgaagtgc agcatttc                                                   18

<210> SEQ ID NO 42
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 42
atctgaagtg cagcattt                                                   18

<210> SEQ ID NO 43
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 43
aataaataag aatatttt                                                   18

<210> SEQ ID NO 44
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 44
gatctgaagt gcagcatt                                                   18

<210> SEQ ID NO 45
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 45
```
acatctgtga tctgaagt                                                 18

<210> SEQ ID NO 46
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 46
cacatctgtg atctgaag                                                 18

<210> SEQ ID NO 47
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 47
tcacatctgt gatctgaa                                                 18

<210> SEQ ID NO 48
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 48
ttcacatctg tgatctga                                                 18

<210> SEQ ID NO 49
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 49
gcaccaccat agctgatc                                                 18

<210> SEQ ID NO 50
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 50
ggcaccacca tagctgat                                                 18

<210> SEQ ID NO 51
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 51
ttgtagtcgg caccacca                                                 18

<210> SEQ ID NO 52
<211> LENGTH: 18
<212> TYPE: DNA

```
<213> ORGANISM: Artificial Sequence
<220> FEATURE:
<223> OTHER INFORMATION: Synthetic Oligonucleotide

<400> SEQUENCE: 52
cttgtagtcg gcaccacc                                                 18

<210> SEQ ID NO 53
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 53
gtaattcgct tgtagtcg                                                 18

<210> SEQ ID NO 54
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 54
agtaattcgc ttgtagtc                                                 18

<210> SEQ ID NO 55
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 55
tggggcattg actttcac                                                 18

<210> SEQ ID NO 56
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 56
atggggcatt gactttca                                                 18

<210> SEQ ID NO 57
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 57
tatggggcat tgactttc                                                 18

<210> SEQ ID NO 58
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 58
gtatggggca ttgacttt                                                 18
```

-continued

<210> SEQ ID NO 59
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 59
tgtatggggc attgactt                                                 18

<210> SEQ ID NO 60
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 60
ttgtatgggg cattgact                                                 18

<210> SEQ ID NO 61
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 61
gttgtatggg gcattgac                                                 18

<210> SEQ ID NO 62
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 62
tgttgtatgg ggcattga                                                 18

<210> SEQ ID NO 63
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 63
ttgttgtatg gggcattg                                                 18

<210> SEQ ID NO 64
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 64
tttgttgtat ggggcatt                                                 18

<210> SEQ ID NO 65
<211> LENGTH: 18
<212> TYPE: DNA
<213> ORGANISM: Artificial Sequence
<220> FEATURE:

<223> OTHER INFORMATION: Synthetic Oligonucleotide

<400> SEQUENCE: 65
ttttgttgta tggggcat                                          18

<210> SEQ ID NO 66
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 66
attttgttgt atggggca                                          18

<210> SEQ ID NO 67
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 67
gattttgttg tatggggc                                          18

<210> SEQ ID NO 68
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 68
tgattttgtt gtatgggg                                          18

<210> SEQ ID NO 69
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 69
ttctttggtt gattttgt                                          18

<210> SEQ ID NO 70
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 70
attctttggt tgattttg                                          18

<210> SEQ ID NO 71
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 71
aattctttgg ttgatttt                                          18

```
<210> SEQ ID NO 72
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 72
aaattctttg gttgattt                                                 18

<210> SEQ ID NO 73
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 73
aaaattcttt ggttgatt                                                 18

<210> SEQ ID NO 74
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 74
agaggtgact ggatccac                                                 18

<210> SEQ ID NO 75
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 75
cagaggtgac tggatcca                                                 18

<210> SEQ ID NO 76
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 76
tcagaggtga ctggatcc                                                 18

<210> SEQ ID NO 77
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 77
ctgacatgtc agttcatg                                                 18

<210> SEQ ID NO 78
<211> LENGTH: 18
<212> TYPE: DNA
<213> ORGANISM: Artificial Sequence
<220> FEATURE:
<223> OTHER INFORMATION: Synthetic Oligonucleotide
```

<400> SEQUENCE: 78
tagccctcag cctgacat                                                 18

<210> SEQ ID NO 79
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 79
tcactgcttg tccagatg                                                 18

<210> SEQ ID NO 80
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 80
gtcactgctt gtccagat                                                 18

<210> SEQ ID NO 81
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 81
ggtcactgct tgtccaga                                                 18

<210> SEQ ID NO 82
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 82
tggtcactgc ttgtccag                                                 18

<210> SEQ ID NO 83
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 83
gtgtgctggt cacattga                                                 18

<210> SEQ ID NO 84
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 84
agtgtgctgg tcacattg                                                 18

<210> SEQ ID NO 85
<211> LENGTH: 18

```
<212> TYPE: DNA
<213> ORGANISM: Artificial Sequence
<220> FEATURE:
<223> OTHER INFORMATION: Synthetic Oligonucleotide

<400> SEQUENCE: 85
cagtgtgctg gtcacatt                                                  18

<210> SEQ ID NO 86
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 86
tcagtgtgct ggtcacat                                                  18

<210> SEQ ID NO 87
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 87
ctcagtgtgc tggtcaca                                                  18

<210> SEQ ID NO 88
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 88
aggtagttct gggatgac                                                  18

<210> SEQ ID NO 89
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 89
gaggtagttc tgggatga                                                  18

<210> SEQ ID NO 90
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 90
tctttgagtt tgtatctt                                                  18

<210> SEQ ID NO 91
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 91
```
ttctttgagt ttgtatct                                              18

<210> SEQ ID NO 92
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 92
tcctccaaat gtgtatca                                              18

<210> SEQ ID NO 93
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 93
ctcctccaaa tgtgtatc                                              18

<210> SEQ ID NO 94
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 94
gacagcaaat atcctcatc                                             19

<210> SEQ ID NO 95
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 95
agacagcaaa tatcctcat                                             19

<210> SEQ ID NO 96
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 96
aagacagcaa atatcctca                                             19

<210> SEQ ID NO 97
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 97
aaagacagca aatatcctc                                             19

<210> SEQ ID NO 98
<211> LENGTH: 19
<212> TYPE: DNA
<213> ORGANISM: Artificial Sequence

```
<220> FEATURE:
<223> OTHER INFORMATION: Synthetic Oligonucleotide

<400> SEQUENCE: 98
taaagacagc aaatatcct                                              19

<210> SEQ ID NO 99
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 99
ataaagacag caaatatcc                                              19

<210> SEQ ID NO 100
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 100
tataaagaca gcaaatatc                                              19

<210> SEQ ID NO 101
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 101
atataaagac agcaaatat                                              19

<210> SEQ ID NO 102
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 102
aatataaaga cagcaaata                                              19

<210> SEQ ID NO 103
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 103
gaatataaag acagcaaat                                              19

<210> SEQ ID NO 104
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 104
cagactcaaa ataaatagg                                              19
```

```
<210> SEQ ID NO 105
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 105
acagactcaa aataaatag                                                19

<210> SEQ ID NO 106
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 106
cacagactca aaataaata                                                19

<210> SEQ ID NO 107
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 107
tcacagactc aaaataaat                                                19

<210> SEQ ID NO 108
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 108
ctcacagact caaaataaa                                                19

<210> SEQ ID NO 109
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 109
cctcacagac tcaaaataa                                                19

<210> SEQ ID NO 110
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 110
acctcacaga ctcaaaata                                                19

<210> SEQ ID NO 111
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 111
gacctcacag actcaaaat                                               19

<210> SEQ ID NO 112
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 112
agacctcaca gactcaaaa                                               19

<210> SEQ ID NO 113
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 113
gataacttag aaacaaaga                                               19

<210> SEQ ID NO 114
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 114
agataactta gaaacaaag                                               19

<210> SEQ ID NO 115
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 115
gggtagctag cagtcaagg                                               19

<210> SEQ ID NO 116
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 116
agggtagcta gcagtcaag                                               19

<210> SEQ ID NO 117
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 117
cagggtagct agcagtcaa                                               19

<210> SEQ ID NO 118
```

```
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 118
cttcagcctt gacatgtgg                                             19

<210> SEQ ID NO 119
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 119
tcttcagcct tgacatgtg                                             19

<210> SEQ ID NO 120
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 120
ttcttcagcc ttgacatgt                                             19

<210> SEQ ID NO 121
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 121
tttcttcagc cttgacatg                                             19

<210> SEQ ID NO 122
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 122
gtttcttcag ccttgacat                                             19

<210> SEQ ID NO 123
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 123
tgaagtgcag catttccca                                             19

<210> SEQ ID NO 124
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 124
```
ctgaagtgca gcatttccc                                    19

<210> SEQ ID NO 125
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 125
tctgaagtgc agcatttcc                                    19

<210> SEQ ID NO 126
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 126
ttttattaaa ttaatgcag                                    19

<210> SEQ ID NO 127
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 127
attttattaa attaatgca                                    19

<210> SEQ ID NO 128
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 128
atctgaagtg cagcatttc                                    19

<210> SEQ ID NO 129
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 129
gatctgaagt gcagcattt                                    19

<210> SEQ ID NO 130
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 130
tgatctgaag tgcagcatt                                    19

<210> SEQ ID NO 131
<211> LENGTH: 19
<212> TYPE: DNA

```
<213> ORGANISM: Artificial Sequence
<220> FEATURE:
<223> OTHER INFORMATION: Synthetic Oligonucleotide

<400> SEQUENCE: 131
tcacatctgt gatctgaag                                                  19

<210> SEQ ID NO 132
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 132
ttcacatctg tgatctgaa                                                  19

<210> SEQ ID NO 133
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 133
cggcaccacc atagctgat                                                  19

<210> SEQ ID NO 134
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 134
cttgtagtcg gcaccacca                                                  19

<210> SEQ ID NO 135
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 135
gcttgtagtc ggcaccacc                                                  19

<210> SEQ ID NO 136
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 136
atggggcatt gactttcac                                                  19

<210> SEQ ID NO 137
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 137
tatggggcat tgactttca                                                  19
```

<210> SEQ ID NO 138
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 138
gtatggggca ttgactttc                                                19

<210> SEQ ID NO 139
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 139
tgtatggggc attgacttt                                                19

<210> SEQ ID NO 140
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 140
ttgtatgggg cattgactt                                                19

<210> SEQ ID NO 141
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 141
gttgtatggg gcattgact                                                19

<210> SEQ ID NO 142
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 142
tgttgtatgg ggcattgac                                                19

<210> SEQ ID NO 143
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 143
ttgttgtatg gggcattga                                                19

<210> SEQ ID NO 144
<211> LENGTH: 19
<212> TYPE: DNA
<213> ORGANISM: Artificial Sequence
<220> FEATURE:

<223> OTHER INFORMATION: Synthetic Oligonucleotide

<400> SEQUENCE: 144
tttgttgtat ggggcattg            19

<210> SEQ ID NO 145
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 145
ttttgttgta tggggcatt            19

<210> SEQ ID NO 146
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 146
attttgttgt atggggcat            19

<210> SEQ ID NO 147
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 147
gattttgttg tatggggca            19

<210> SEQ ID NO 148
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 148
tgattttgtt gtatggggc            19

<210> SEQ ID NO 149
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 149
ttgattttgt tgtatgggg            19

<210> SEQ ID NO 150
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 150
attctttggt tgattttgt            19

```
<210> SEQ ID NO 151
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 151
aattctttgg ttgattttg                                          19

<210> SEQ ID NO 152
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 152
aaattctttg gttgatttt                                          19

<210> SEQ ID NO 153
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 153
aaaattcttt ggttgattt                                          19

<210> SEQ ID NO 154
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 154
cagaggtgac tggatccac                                          19

<210> SEQ ID NO 155
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 155
tcagaggtga ctggatcca                                          19

<210> SEQ ID NO 156
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 156
cctgacatgt cagttcatg                                          19

<210> SEQ ID NO 157
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 157
gtcactgctt gtccagatg                                                    19

<210> SEQ ID NO 158
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 158
ggtcactgct tgtccagat                                                    19

<210> SEQ ID NO 159
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 159
tggtcactgc ttgtccaga                                                    19

<210> SEQ ID NO 160
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 160
atggtcactg cttgtccag                                                    19

<210> SEQ ID NO 161
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 161
agtgtgctgg tcacattga                                                    19

<210> SEQ ID NO 162
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 162
cagtgtgctg gtcacattg                                                    19

<210> SEQ ID NO 163
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 163
tcagtgtgct ggtcacatt                                                    19

<210> SEQ ID NO 164
<211> LENGTH: 19
```

```
<212> TYPE: DNA
<213> ORGANISM: Artificial Sequence
<220> FEATURE:
<223> OTHER INFORMATION: Synthetic Oligonucleotide

<400> SEQUENCE: 164
ctcagtgtgc tggtcacat                                                19

<210> SEQ ID NO 165
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 165
ttctttgagt ttgtatctt                                                19

<210> SEQ ID NO 166
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 166
ctcctccaaa tgtgtatca                                                19

<210> SEQ ID NO 167
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 167
tctcctccaa atgtgtatc                                                19

<210> SEQ ID NO 168
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 168
aagacagcaa atatcctcat                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 169
aaagacagca aatatcctca                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 170
```
taaagacagc aaatatcctc                                              20

<210> SEQ ID NO 171
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 171
ataaagacag caaatatcct                                              20

<210> SEQ ID NO 172
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 172
tataaagaca gcaaatatcc                                              20

<210> SEQ ID NO 173
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 173
atataaagac agcaaatatc                                              20

<210> SEQ ID NO 174
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 174
aatataaaga cagcaaatat                                              20

<210> SEQ ID NO 175
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 175
gaatataaag acagcaaata                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 176
tgaatataaa gacagcaaat                                              20

<210> SEQ ID NO 177
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 177
acagactcaa aataaatagg                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 178
cacagactca aataaatag                                               20

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 179
tcacagactc aaaataaata                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 180
ctcacagact caaaataaat                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 181
cctcacagac tcaaaataaa                                              20

<210> SEQ ID NO 182
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 182
acctcacaga ctcaaaataa                                              20

<210> SEQ ID NO 183
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 183
gacctcacag actcaaaata                                              20
```

```
<210> SEQ ID NO 184
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 184
agacctcaca gactcaaaat                                                 20

<210> SEQ ID NO 185
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 185
agataactta gaaacaaaga                                                 20

<210> SEQ ID NO 186
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 186
agggtagcta gcagtcaagg                                                 20

<210> SEQ ID NO 187
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 187
cagggtagct agcagtcaag                                                 20

<210> SEQ ID NO 188
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 188
ttcttcagcc ttgacatgtg                                                 20

<210> SEQ ID NO 189
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 189
tttcttcagc cttgacatgt                                                 20

<210> SEQ ID NO 190
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 190
gtttcttcag ccttgacatg                                                    20

<210> SEQ ID NO 191
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 191
tgtttcttca gccttgacat                                                    20

<210> SEQ ID NO 192
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 192
ctgaagtgca gcatttccca                                                    20

<210> SEQ ID NO 193
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 193
tctgaagtgc agcatttccc                                                    20

<210> SEQ ID NO 194
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 194
atctgaagtg cagcatttcc                                                    20

<210> SEQ ID NO 195
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 195
gatctgaagt gcagcatttc                                                    20

<210> SEQ ID NO 196
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 196
tgatctgaag tgcagcattt                                                    20

<210> SEQ ID NO 197

-continued

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 197
gtgatctgaa gtgcagcatt                                              20

<210> SEQ ID NO 198
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 198
ttcacatctg tgatctgaag                                              20

<210> SEQ ID NO 199
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 199
tcggcaccac catagctgat                                              20

<210> SEQ ID NO 200
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 200
gcttgtagtc ggcaccacca                                              20

<210> SEQ ID NO 201
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 201
cgcttgtagt cggcaccacc                                              20

<210> SEQ ID NO 202
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 202
tatggggcat tgactttcac                                              20

<210> SEQ ID NO 203
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 203
``` gtatgggca ttgactttca    20

<210> SEQ ID NO 204
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 204
tgtatggggc attgactttc    20

<210> SEQ ID NO 205
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 205
ttgtatgggg cattgacttt    20

<210> SEQ ID NO 206
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 206
gttgtatggg gcattgactt    20

<210> SEQ ID NO 207
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 207
tgttgtatgg ggcattgact    20

<210> SEQ ID NO 208
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 208
ttgttgtatg gggcattgac    20

<210> SEQ ID NO 209
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 209
tttgttgtat ggggcattga    20

<210> SEQ ID NO 210
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 210
ttttgttgta tggggcattg                                            20

<210> SEQ ID NO 211
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 211
attttgttgt atgggcatt                                             20

<210> SEQ ID NO 212
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 212
gattttgttg tatggggcat                                            20

<210> SEQ ID NO 213
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 213
tgattttgtt gtatggggca                                            20

<210> SEQ ID NO 214
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 214
ttgattttgt tgtatggggc                                            20

<210> SEQ ID NO 215
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 215
gttgattttg ttgtatgggg                                            20

<210> SEQ ID NO 216
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 216
aattctttgg ttgattttgt                                            20
```

```
<210> SEQ ID NO 217
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 217
aaattctttg gttgattttg                                              20

<210> SEQ ID NO 218
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 218
aaaattcttt ggttgatttt                                              20

<210> SEQ ID NO 219
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 219
tcagaggtga ctggatccac                                              20

<210> SEQ ID NO 220
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 220
gcctgacatg tcagttcatg                                              20

<210> SEQ ID NO 221
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 221
ggtcactgct tgtccagatg                                              20

<210> SEQ ID NO 222
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 222
tggtcactgc ttgtccagat                                              20

<210> SEQ ID NO 223
<211> LENGTH: 20
<212> TYPE: DNA
<213> ORGANISM: Artificial Sequence
<220> FEATURE:
```

<223> OTHER INFORMATION: Synthetic Oligonucleotide

<400> SEQUENCE: 223
atggtcactg cttgtccaga                                         20

<210> SEQ ID NO 224
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 224
gatggtcact gcttgtccag                                         20

<210> SEQ ID NO 225
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 225
cagtgtgctg gtcacattga                                         20

<210> SEQ ID NO 226
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 226
tcagtgtgct ggtcacattg                                         20

<210> SEQ ID NO 227
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 227
ctcagtgtgc tggtcacatt                                         20

<210> SEQ ID NO 228
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 228
tctcctccaa atgtgtatca                                         20

<210> SEQ ID NO 229
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 229
gtctcctcca aatgtgtatc                                         20

```
<210> SEQ ID NO 230
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 230
aaagacagca aatatcctca t                                              21

<210> SEQ ID NO 231
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 231
taaagacagc aaatatcctc a                                              21

<210> SEQ ID NO 232
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 232
ataaagacag caaatatcct c                                              21

<210> SEQ ID NO 233
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 233
tataaagaca gcaaatatcc t                                              21

<210> SEQ ID NO 234
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 234
atataaagac agcaaatatc c                                              21

<210> SEQ ID NO 235
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 235
aatataaaga cagcaaatat c                                              21

<210> SEQ ID NO 236
<211> LENGTH: 21
<212> TYPE: DNA
<213> ORGANISM: Artificial Sequence
<220> FEATURE:
<223> OTHER INFORMATION: Synthetic Oligonucleotide
```

<400> SEQUENCE: 236
gaatataaag acagcaaata t                                             21

<210> SEQ ID NO 237
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 237
tgaatataaa gacagcaaat a                                             21

<210> SEQ ID NO 238
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 238
cacagactca aaataaatag g                                             21

<210> SEQ ID NO 239
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 239
tcacagactc aaaataaata g                                             21

<210> SEQ ID NO 240
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 240
ctcacagact caaaataaat a                                             21

<210> SEQ ID NO 241
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 241
cctcacagac tcaaaataaa t                                             21

<210> SEQ ID NO 242
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 242
acctcacaga ctcaaaataa a                                             21

<210> SEQ ID NO 243
<211> LENGTH: 21

```
<212> TYPE: DNA
<213> ORGANISM: Artificial Sequence
<220> FEATURE:
<223> OTHER INFORMATION: Synthetic Oligonucleotide

<400> SEQUENCE: 243
gacctcacag actcaaaata a                                              21

<210> SEQ ID NO 244
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 244
agacctcaca gactcaaaat a                                              21

<210> SEQ ID NO 245
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 245
cagggtagct agcagtcaag g                                              21

<210> SEQ ID NO 246
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 246
tttcttcagc cttgacatgt g                                              21

<210> SEQ ID NO 247
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 247
gtttcttcag ccttgacatg t                                              21

<210> SEQ ID NO 248
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 248
tgtttcttca gccttgacat g                                              21

<210> SEQ ID NO 249
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 249
```
ctgtttcttc agccttgaca t                                              21

<210> SEQ ID NO 250
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 250
tctgaagtgc agcatttccc a                                              21

<210> SEQ ID NO 251
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 251
atctgaagtg cagcatttcc c                                              21

<210> SEQ ID NO 252
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 252
gatctgaagt gcagcatttc c                                              21

<210> SEQ ID NO 253
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 253
tgatctgaag tgcagcattt c                                              21

<210> SEQ ID NO 254
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 254
gtgatctgaa gtgcagcatt t                                              21

<210> SEQ ID NO 255
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 255
tgtgatctga agtgcagcat t                                              21

<210> SEQ ID NO 256
<211> LENGTH: 21
<212> TYPE: DNA
<213> ORGANISM: Artificial Sequence

```
<220> FEATURE:
<223> OTHER INFORMATION: Synthetic Oligonucleotide

<400> SEQUENCE: 256
gtcggcacca ccatagctga t                                              21

<210> SEQ ID NO 257
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 257
cgcttgtagt cggcaccacc a                                              21

<210> SEQ ID NO 258
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 258
tcgcttgtag tcggcaccac c                                              21

<210> SEQ ID NO 259
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 259
gtatggggca ttgactttca c                                              21

<210> SEQ ID NO 260
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 260 tgtatgggc attgactttc a                                               21

<210> SEQ ID NO 261
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 261
ttgtatgggg cattgacttt c                                              21

<210> SEQ ID NO 262
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 262
gttgtatggg gcattgactt t                                              21
```

<210> SEQ ID NO 263
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 263
tgttgtatgg ggcattgact t                                         21

<210> SEQ ID NO 264
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 264
ttgttgtatg gggcattgac t                                         21

<210> SEQ ID NO 265
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 265
tttgttgtat ggggcattga c                                         21

<210> SEQ ID NO 266
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 266
ttttgttgta tggggcattg a                                         21

<210> SEQ ID NO 267
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 267
attttgttgt atggggcatt g                                         21

<210> SEQ ID NO 268
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 268
gattttgttg tatggggcat t                                         21

<210> SEQ ID NO 269
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 269
tgattttgtt gtatggggca t                                              21

<210> SEQ ID NO 270
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 270
ttgattttgt tgtatgggc a                                               21

<210> SEQ ID NO 271
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 271
gttgattttg ttgtatgggg c                                              21

<210> SEQ ID NO 272
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 272
ggttgatttt gttgtatggg g                                              21

<210> SEQ ID NO 273
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 273
aaattctttg gttgattttg t                                              21

<210> SEQ ID NO 274
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 274
aaaattcttt ggttgatttt g                                              21

<210> SEQ ID NO 275
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 275
tggtcactgc ttgtccagat g                                              21

<210> SEQ ID NO 276

```
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 276
atggtcactg cttgtccaga t                                              21

<210> SEQ ID NO 277
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 277
gatggtcact gcttgtccag a                                              21

<210> SEQ ID NO 278
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 278
tgatggtcac tgcttgtcca g                                              21

<210> SEQ ID NO 279
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 279
tcagtgtgct ggtcacattg a                                              21

<210> SEQ ID NO 280
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 280
ctcagtgtgc tggtcacatt g                                              21

<210> SEQ ID NO 281
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 281
gtctcctcca aatgtgtatc a                                              21

<210> SEQ ID NO 282
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 282
```
cgtctcctcc aaatgtgtat c                                              21

<210> SEQ ID NO 283
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 283
aagcgcggct ggtgcggag                                                 19

<210> SEQ ID NO 284
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 284
aatgccctgc aggcggaca                                                 19

<210> SEQ ID NO 285
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 285
cgttcagcaa atgccagta                                                 19

<210> SEQ ID NO 286
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 286
gggaaccgtg acagtaaat                                                 19

<210> SEQ ID NO 287
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 287
tctaccacat ataggtcct                                                 19

<210> SEQ ID NO 288
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 288
ttgtcatatt gctaccata                                                 19

<210> SEQ ID NO 289
<211> LENGTH: 19
<212> TYPE: DNA

```
<213> ORGANISM: Artificial Sequence
<220> FEATURE:
<223> OTHER INFORMATION: Synthetic Oligonucleotide

<400> SEQUENCE: 289
tactgggaat ttgcattca                                               19

<210> SEQ ID NO 290
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 290
gccaggtcta attgttttt                                               19

<210> SEQ ID NO 291
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 291
cccaatagac aattagtgc                                               19

<210> SEQ ID NO 292
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 292
tctccatgca caaattgaa                                               19

<210> SEQ ID NO 293
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 293
gctgaacctt caggtcttc                                               19

<210> SEQ ID NO 294
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 294
cctctgtctg tagctacta                                               19

<210> SEQ ID NO 295
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 295
tggtccttca acagccggg                                               19
```

<210> SEQ ID NO 296
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 296
ttcggccttg gggtagccc                                                   19

<210> SEQ ID NO 297
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 297
ggaattggtg gtggtggtc                                                   19

<210> SEQ ID NO 298
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 298
caattcagct gtatggttt                                                   19

<210> SEQ ID NO 299
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 299
tttcatttgg aggatgtgc                                                   19

<210> SEQ ID NO 300
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 300
aggcataata agatggctc                                                   19

<210> SEQ ID NO 301
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 301
tgaatgtcag tgctacacc                                                   19

<210> SEQ ID NO 302
<211> LENGTH: 19
<212> TYPE: DNA
<213> ORGANISM: Artificial Sequence
<220> FEATURE:

<223> OTHER INFORMATION: Synthetic Oligonucleotide

<400> SEQUENCE: 302
ccctttcttt aaacggaag                                                 19

<210> SEQ ID NO 303
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 303
tttttcacat ccatcattc                                                 19

<210> SEQ ID NO 304
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 304
gagaatccct gcttgaaga                                                 19

<210> SEQ ID NO 305
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 305 gaaccctaa accacaggt                                                  19

<210> SEQ ID NO 306
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 306
tcagtgcttg ggcctttta                                                 19

<210> SEQ ID NO 307
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 307
gctttcgcca ggttccatt                                                 19

<210> SEQ ID NO 308
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 308
ccctgtcaca ggcgtcgat                                                 19

```
<210> SEQ ID NO 309
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 309
tgttcagaag tatcctttc                                                19

<210> SEQ ID NO 310
<211> LENGTH: 19
<212> TYPE: DNA
<213> ORGANISM: Artificial Sequence
<220> FEATURE:
<223> OTHER INFORMATION: Nucleuic acid

<400> SEQUENCE: 310
ttagggattc tcaacccgt                                                19

<210> SEQ ID NO 311
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 311
tgcaggaact gaccctcaa                                                19

<210> SEQ ID NO 312
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 312
aaaacaaatt gaggcattg                                                19

<210> SEQ ID NO 313
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 313
atactgtccc gttccaaca                                                19

<210> SEQ ID NO 314
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 314
aaaagaaatc attcacaac                                                19

<210> SEQ ID NO 315
<211> LENGTH: 19
<212> TYPE: DNA
<213> ORGANISM: Artificial Sequence
<220> FEATURE:
<223> OTHER INFORMATION: Synthetic Oligonucleotide
```

<400> SEQUENCE: 315
tttggcgaca aaattgtaa                                            19

<210> SEQ ID NO 316
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 316
tcattaagca gcaagttta                                            19

<210> SEQ ID NO 317
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 317
caccttacaa atactccat                                            19

<210> SEQ ID NO 318
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 318
atgcttccaa tgtatactt                                            19

<210> SEQ ID NO 319
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 319
caaccaacgg tttgatctt                                            19

<210> SEQ ID NO 320
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 320
aataaaggtg acatcctat                                            19

<210> SEQ ID NO 321
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 321
actgcacaga cacttgagg                                            19

<210> SEQ ID NO 322
<211> LENGTH: 19

```
<212> TYPE: DNA
<213> ORGANISM: Artificial Sequence
<220> FEATURE:
<223> OTHER INFORMATION: Synthetic Oligonucleotide

<400> SEQUENCE: 322
gatatttaaa tggaacaga                                                19

<210> SEQ ID NO 323
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 323
taccacataa ttgtaaagc                                                19

<210> SEQ ID NO 324
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 324
atgagattat gtgtgtagg                                                19

<210> SEQ ID NO 325
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 325
atttactggt ttgggcaag                                                19

<210> SEQ ID NO 326
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 326
gtggcagtct gaggtctgc                                                19

<210> SEQ ID NO 327
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 327
gtattataaa aggacagtg                                                19

<210> SEQ ID NO 328
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 328
```

```
gtaaaatata gctgtaaat                                                  19

<210> SEQ ID NO 329
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 329
gaataaaaga attgcttaa                                                  19

<210> SEQ ID NO 330
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 330
gcacttaata aatggtttt                                                  19

<210> SEQ ID NO 331
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 331
cagcgattga tattgcaag                                                  19

<210> SEQ ID NO 332
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 332
tactttgtct tgctcacat                                                  19

<210> SEQ ID NO 333
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 333
gttaatctcc tcattatac                                                  19

<210> SEQ ID NO 334
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 334
tgctatgaca ctggactaa                                                  19

<210> SEQ ID NO 335
<211> LENGTH: 19
<212> TYPE: DNA
<213> ORGANISM: Artificial Sequence
```

```
<220> FEATURE:
<223> OTHER INFORMATION: Synthetic Oligonucleotide

<400> SEQUENCE: 335
ttggcaacac tgctcgggt                                              19

<210> SEQ ID NO 336
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 336
tatccaaccg tcccagacc                                              19

<210> SEQ ID NO 337
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 337
tgtaaatgaa aattactct                                              19

<210> SEQ ID NO 338
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 338
tttaagtacc gacctctct                                              19

<210> SEQ ID NO 339
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 339
atgctagaaa aggaattcc                                              19

<210> SEQ ID NO 340
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 340
gcaaatcagg aataaatat                                              19

<210> SEQ ID NO 341
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 341
ccagacacta tataaacaa                                              19
```

-continued

<210> SEQ ID NO 342
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 342
gacagaactg ttaaacaat                                              19

<210> SEQ ID NO 343
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 343
aaggtatgaa tttaaaatt                                              19

<210> SEQ ID NO 344
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 344
aaccatctcc catgggatc                                              19

<210> SEQ ID NO 345
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 345
ggatgaagtg gagattttc                                              19

<210> SEQ ID NO 346
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 346
ggaaacttga atggcttgg                                              19

<210> SEQ ID NO 347
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 347
gtagcagttg cttctggaa                                              19

<210> SEQ ID NO 348
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 348
gaacatatga atgaaaggc                                            19

<210> SEQ ID NO 349
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 349
aaaaaatttt aaaaatacg                                            19

<210> SEQ ID NO 350
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 350
caatgtgtta ctatttagg                                            19

<210> SEQ ID NO 351
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 351
ccatctgcta tataagaaa                                            19

<210> SEQ ID NO 352
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 352
ctgggaactt caaattcat                                            19

<210> SEQ ID NO 353
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 353
agataatgaa aagctatgg                                            19

<210> SEQ ID NO 354
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 354
catatactgg atcatatga                                            19

<210> SEQ ID NO 355

```
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 355
tatatgtagg acatattta                                          19

<210> SEQ ID NO 356
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 356
aaatggtggt tgtctaaat                                          19

<210> SEQ ID NO 357
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 357
tcctagagca aatacttaa                                          19

<210> SEQ ID NO 358
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 358
ataaacaaat ccaaactct                                          19

<210> SEQ ID NO 359
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 359
gtgcaccctg gagagccca                                          19

<210> SEQ ID NO 360
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 360
tttaggacta gattgactc                                          19

<210> SEQ ID NO 361
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 361
```
agttaataat aagattgct                                          19

<210> SEQ ID NO 362
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 362
gacatgattc tgtcataca                                          19

<210> SEQ ID NO 363
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 363
agcagaaaac aaaagttcc                                          19

<210> SEQ ID NO 364
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 364
tgcaagtaca gcatcaaag                                          19

<210> SEQ ID NO 365
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 365
ccagaaagaa aatgtgatt                                          19

<210> SEQ ID NO 366
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 366
caacgaatga ggcttttct                                          19

<210> SEQ ID NO 367
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 367
ggcattcaag ggttcaagc                                          19

<210> SEQ ID NO 368
<211> LENGTH: 19
<212> TYPE: DNA

<213> ORGANISM: Artificial Sequence
<220> FEATURE:
<223> OTHER INFORMATION: Synthetic Oligonucleotide

<400> SEQUENCE: 368
gtgtagtgat gacagctgg                                    19

<210> SEQ ID NO 369
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 369
tggccaagag ggaaaggaa                                    19

<210> SEQ ID NO 370
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 370
ttgtcattga caccagaat                                    19

<210> SEQ ID NO 371
<211> LENGTH: 19
<212> TYPE: DNA
<213> ORGANISM: Artificial Sequence
<220> FEATURE:
<223> OTHER INFORMATION: Nucleiuc acid

<400> SEQUENCE: 371
ggagctctgt tggagacac                                    19

<210> SEQ ID NO 372
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 372
tgtacaaaca gataacaca                                    19

<210> SEQ ID NO 373
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 373
acaaagaaca ctgtcacac                                    19

<210> SEQ ID NO 374
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 374
aattcttgcc tgtaattca                                    19

<210> SEQ ID NO 375
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 375
taggaataga ctgagtaga                                                19

<210> SEQ ID NO 376
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 376
gtgccttaca aatccaaca                                                19

<210> SEQ ID NO 377
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 377
catgagacaa aagggataa                                                19

<210> SEQ ID NO 378
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 378
ctatgccatt tacgatgaa                                                19

<210> SEQ ID NO 379
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 379
atgctggtgt accaagtaa                                                19

<210> SEQ ID NO 380
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 380
tgaacatttt attaaacac                                                19

METHODS AND COMPOSITIONS FOR TARGETING PD-L1

INCORPORATION BY REFERENCE TO PRIORITY APPLICATION

This application claims priority to U.S. Provisional Application Ser. No. 62/983,114, filed Feb. 28, 2020, which is hereby incorporated herein by reference in its entirety.

REFERENCE TO SEQUENCE LISTING

The present application is being filed along with a Sequence Listing in electronic format. The Sequence Listing is provided as a file entitled SEQ LISTING ALIG.036A created Apr. 27, 2021, which is approximately 74 KB in size. The information in the electronic format of the Sequence Listing is incorporated herein by reference in its entirety.

FIELD

The present application relates to the fields of chemistry, biochemistry, molecular biology and medicine. The present disclosure relates to small interfering RNA (siRNA) molecules directed to mRNA transcripts of CD274 to cause downregulation of programmed death-ligand 1 (PD-L1) expression in humans. The siRNA can be constructed of unmodified nucleotides or modified nucleotides that exhibit modified sugars, nucleobases, linkages, or covalently bound targeting and/or lipophilic moieties. Also disclosed herein are pharmaceutical compositions of siRNAs and uses of or methods of using the siRNAs for the treatment of PD-L1 related diseases including but not limited to liver diseases, cancer, hepatocellular carcinoma, viral diseases, or hepatitis B.

BACKGROUND

The programmed cell death 1 (PD-1) immune checkpoint expressed on the surface of activated CD4+ and CD8+ T cells controls an inhibitory mechanism to prevent autoimmunity. Engagement of PD-1 by programmed death-ligand 1 (PD-L1) expressed on the multitude of cell types, including macrophages, dendritic cells, mast cells as well as non-hematopoietic cells, induces T cell exhaustion resulting in reduction or loss of effector cytokine production (e.g. IL-2, TNF-α, IFN-γ) and upregulation of other inhibitory receptors and immune checkpoints (e.g. CTLA-4, LAG-3, and BTLA), or T cell apoptosis. High expression of PD-L1 is exhibited by many types of cancers to escape tumor immune surveillance and has been associated with poorer prognosis. PD-1-mediated immunosuppression is also linked to some viral infections, such as hepatitis B. There is an ongoing need for PD-1/PD-L1 therapies and improvements thereof for the treatment of disease.

SUMMARY

Embodiments provided herein related to small interfering RNA (siRNA) molecules that target to CD274, compositions thereof, and uses thereof for the treatment, inhibition, amelioration, prevention or slowing of diseases or conditions associated with PD-L1 dysregulation.

Some embodiments provided herein relate to small interfering RNAs (siRNAs) that targets human CD274 mRNA. In some embodiments, the siRNA comprises a sense strand and an antisense strand. In some embodiments, the antisense strand comprises 18 to 21 nucleotides selected from the group consisting of unmodified nucleotides and modified nucleosides. In some embodiments, each modified nucleoside contains a modified sugar, contains a modified nucleobase or is abasic, or both contains a modified sugar and contains a modified nucleobase or is abasic. In some embodiments, each linkage between the nucleosides is a phosphorothioate, phosphodiester, phosphoramidate, thiophosphoramidate, methylphosphate, methylphosphonate, boranophosphate, or any combination thereof. In some embodiments, the siRNA is at least 85% complementary to a fragment of human CD274 mRNA. In some embodiments, the siRNA comprises zero, one, or two mismatches to the fragment of human CD274 mRNA. In some embodiments, the mismatches occur at any one or more of positions 1 or 9 through m, wherein m is the total number of nucleotides in the antisense strand. In some embodiments, the mismatches do not occur at a seed region of the siRNA. In some embodiments, the seed region is at positions 2-8. In some embodiments, the siRNA has a sequence as set forth in any one of SEQ ID NOs: 2-380. In some embodiments, the siRNA has 18 nucleotides. In some embodiments, the siRNA has 19 nucleotides. In some embodiments, the siRNA has 20 nucleotides. In some embodiments, the siRNA has 21 nucleotides. In some embodiments, the siRNA includes a 2-nucleotide overhang. In some embodiments, the 2-nucleotide overhang is non-complementary to the CD274 mRNA. In some embodiments, the modified sugar is selected from the group consisting of 2'-OMe, 2'-F, 2'-MOE, 2'-araF, 2'-OEt, 2'-O-alkyl, LNA, scpBNA, AmNA, cEt, ENA, and GNA. In some embodiments, the antisense strand comprises a 5'-phosphate group or a 5'-phosphate mimic. In some embodiments, the 5'-phosphate mimic is a 5'-vinylphosphonate.

In some embodiments, the siRNA further includes a targeting and/or lipophilic moiety. In some embodiments, the targeting moiety is conjugated to the siRNA at the 5' end, 3' end, or both. In some embodiments, the targeting moiety is a fatty acid, GalNAc, folic acid, cholesterol, tocopherol, or palmitate. In some embodiments, the siRNA includes a base selected from the group consisting of adenine, guanine, cytosine, thymine, and uracil.

Some embodiments provided herein relate to pharmaceutical compositions. In some embodiments, the compositions include an effective amount of any siRNA described herein and a pharmaceutically acceptable carrier, diluent, excipient, or combination thereof.

Some embodiments provided herein relate to any siRNA as described herein or any pharmaceutical composition as described herein for use in treating a disorder or disease, such as an infection or a cancer, such as for use in treating hepatitis B or for use in treating hepatocellular carcinoma (HCC). In some embodiments, the siRNA is used in combination with surgery, radiation therapy, chemotherapy, targeted therapy, immunotherapy, hormonal therapy, or antiviral therapy. In some embodiments, the siRNA comprises an siRNA against PD-L1 and an siRNA or an antisense oligonucleotide (ASO) against hepatitis B virus (HBV).

Some embodiments provided herein relate to methods for treating a disease or disorder in a subject. In some embodiments, the methods include administering to the subject an effective amount of any siRNA as described herein or an effective amount of any pharmaceutical composition as described herein. In some embodiments, the disease or disorder is an infection or a cancer, such as hepatitis B or hepatocellular carcinoma. In some embodiments, the methods further include administering surgery, radiation therapy, chemotherapy, targeted therapy, immunotherapy, hormonal therapy, or antiviral therapy.

Additional embodiments are described in greater detail below.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments, and are not intended to be limiting in scope.

DETAILED DESCRIPTION

Figure 1:
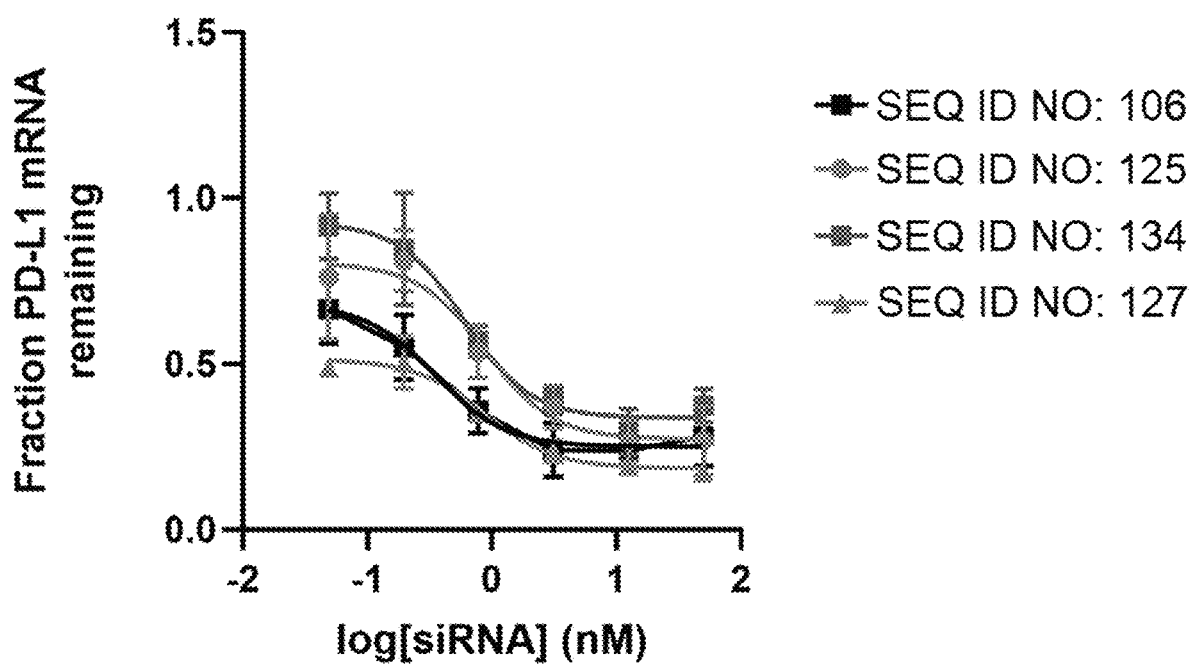
FIG. 1 depicts fraction of PD-L1 mRNA remaining in siRNA treated human hepatocellular carcinoma cells (SNU-387 cells) after treatment with exemplary modified siRNA sequences provided herein.

Unless defined otherwise, all technical and scientific terms used herein have the same meaning as is commonly understood by one of ordinary skill in the art. All patents, applications, published applications and other publications referenced herein are expressly incorporated by reference in their entireties unless stated otherwise. In the event that there is a plurality of definitions for a term herein, those in this section prevail unless stated otherwise.

The articles "a" and "an" are used herein to refer to one or to more than one (for example, at least one) of the grammatical object of the article. By way of example, "an element" means one element or more than one element.

The terms "about" or "around" as used herein refer to a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The practice of the present disclosure will employ, unless indicated specifically to the contrary, conventional methods of molecular biology and recombinant DNA techniques within the skill of the art.

Hepatocellular carcinoma (HCC) is the most common form of liver cancer. HCC can be caused by a variety of conditions, such as alcohol consumption, cirrhosis, and viral infections that cause hepatitis, such as hepatitis B virus, hepatitis C virus, and hepatitis D virus. The inflammation, fibrosis, and cirrhosis linked with these conditions can induce malignancies in affected liver cells. HCC has relatively poor prognosis, with a five-year survival rate of about 30%, depending on if full surgical resection of the tumor is possible.

For early disease, surgical resection is used. However, most HCC are identified at later stages because of difficulties in diagnosing. Upon late stage diagnosis, the tumors are unresectable, and most patients are given systemic therapies. The current standard of care in front line are multi-kinase inhibitors (including, for example, sorafenib and/or lenvatinib). Most patients are refractory or relapse from these treatments, and undergo second line therapies that have anti-angiogenic agents (including, for example, Regorafinib, Cabozantinib, and/or Ramicirumab) or immune checkpoint inhibitors (including, for example, nibolumab and/or pembrolizumab). However, most patients do not respond to first and second therapies, and the clinical benefit is poor, with overall survival not exceeding one year. In addition, biomarker driven therapies are lacking. Thus, there is a need to develop more tolerable and efficacious therapies for the treatment of HCC and related liver disorders.

HBV is a partially double-stranded circular DNA of about 3.2 kilobase (kb) pairs, and is classified into eight genotypes, A to H. The HBV replication pathway has been studied in great detail. One part of replication includes the formation of the covalently closed circular DNA (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of an HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Programmed cell death 1, or programmed death 1 (PD-1) is a 268 amino acid long type I transmembrane protein found as a surface marker on T cells and other immune cells. As an immune checkpoint, PD-1 serves to negatively regulate immune responses to prevent autoimmune disorder. PD-1 protein (NCBI accession number NP_005009.2) is expressed from the cluster of differentiation 279 (CD279) gene (NCBI accession number NG_012110.1) or mRNA transcript (NCBI accession number NM_005018.3). In some preferred embodiments, PD-1 is the human PD-1 protein, and CD279 is the human CD279 transcript or gene on chromosome 2. It should be understood that a person with ordinary skill in the art would view the terms PD-1 and CD279 as often nominally interchangeable when considering the nucleic acid (DNA or RNA) or corresponding translated protein, or the sequences thereof.

Programmed cell death-ligand 1, or programmed death-ligand 1 (PD-L1), also known as B7 homolog 1 (B7-H1) is 272 amino acid long type I transmembrane protein found as a surface marker on many different cell types. PD-L1 is a major ligand of PD-1 and results in inhibition of T cell cytotoxicity and cytokine production. Cancer cells such as HCC cells take advantage of this immune checkpoint by upregulating PD-L1 expression, resulting in dysfunctional anti-tumor immunity by proximal T cells. Viruses also have been observed to modulate the PD-1/PD-L1 pathway to improve infectivity. Hepatitis B virus has been shown to upregulate PD-L1 in infected hepatocytes, and PD-1 in associated T cells. PD-L1 protein (NCBI accession number NP_054862.1) is expressed from the cluster of differentiation 274 (CD274) transcript (NCBI accession number NM_014143.4). In some preferred embodiments, PD-L1 is the human PD-L1 protein, and CD274 is the human CD274 transcript or gene on chromosome 9. It should be understood that a person with ordinary skill in the art would view the terms PD-L1 and CD274 as often nominally interchangeable when considering the nucleic acid (DNA or RNA) or corresponding translated protein, or the sequences thereof.

As used herein, an "oligonucleotide" refers to a single stranded nucleic acid molecule that includes unmodified nucleotides, modified nucleotides or a combination of modified nucleotides and unmodified nucleotides. In the context of siRNA, an oligonucleotide refers to a strand of the siRNA, such as the sense strand (S strand) or the antisense strand (AS strand).

As used herein, an "unmodified nucleotide" is a nucleotide that has a deoxyribose sugar or a ribose sugar and a nucleobase selected from adenine, cytosine, guanine, thymine and uracil. An unmodified nucleotide can also be considered to have a nucleoside selected from cytidine, uridine, 5-methyluridine, guanosine and adenosine, deoxycytidine, deoxyuridine, deoxyguanosine, deoxyadenosine, and thymidine. The structures of deoxyribose, ribose, adenine, cytosine, guanine, thymine, uracil, cytidine, uridine, 5-methyluridine, guanosine, adenosine, deoxycytidine, deoxyuridine, deoxyguanosine, deoxyadenosine, and thymidine are known to those skilled in the art.

As used herein, a "deoxyribose sugar" has the structure

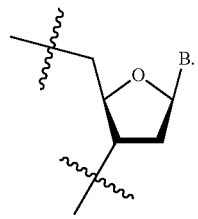

B indicates a nucleobase.

As used herein, a "ribose sugar" has the structure

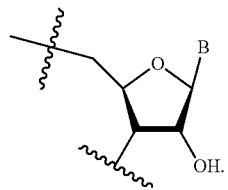

B indicates a nucleobase.

Relevant positions of the 5-membered sugar ring is provided:

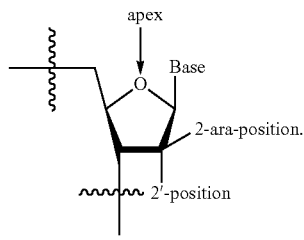

As used herein, "modified nucleoside", or "modified nucleotide" when involving the 3' or 5' linkage, refers to a nucleoside that (a) includes or contains a modified sugar, (b) includes or contains a modified base or is abasic, or (c) both (a) includes or contains a modified deoxyribose and (b) includes or contains a modified base or is abasic. A modified sugar refers to either a modified deoxyribose sugar or modified ribose sugar.

As used herein, the term "modified deoxyribose" refers to a deoxyribose sugar that is substituted at one or more positions with a non-hydrogen substituent. The modifications on the deoxy sugar ring can be at any position of the ring, including at the 2'-carbon. As used herein, the term "modified ribose sugar" refers to a ribose sugar that is substituted at one or more positions with a non-hydrogen substituent. The modifications on the deoxyribose sugar or ribose sugar can be at any position of the ring, including at the 2'-carbon.

Examples of modified sugars include but are not limited to 2'-deoxy-2'-fluoro ribose (2'-F), 2'-deoxy-2'-fluoro-arabinonucloetide (2'-araF), 2'-arabinonucleotide (2'-araOH), 2'-O-methyl ribose (2'-OMe), 2'-O-(2-methoxyethyl) ribose (2'-MOE), locked nucleic acid (LNA), 2'-O-ethyl ribose (2'-OEt), 2'-O-alkyl, (S)-constrained ethyl (cEt), ethylene-bridged nucleic acid (ENA), 4'-C-spirocyclopropylene bridged nucleic acid (scpBNA), amido-bridged nucleic acid (AmNA), unlocked nucleic acid (UNA), and glycol nucleic acid (GNA).

As used herein, "2'-F" refers to a modified deoxyribose sugar that has 2' fluorine substitution and has the structure

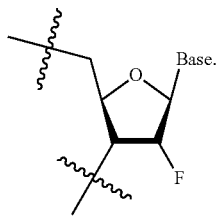

As used herein, "2'-araF" refers to a modified ribose sugar that has a fluorine group attached to 2' position, and has the structure

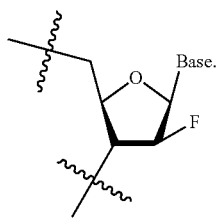

As used herein, "2'-araOH" refers to a modified ribose sugar that has a hydroxy group attached to 2' position, and has the structure

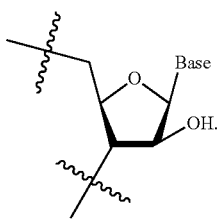

As used herein, "2'-OMe" refers to a modified ribose sugar that has a methyl group attached to the 2' hydroxyl and has the structure

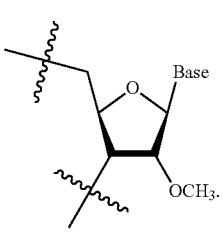

As used herein, "2'-MOE" refers to a modified ribose sugar that has a 2-methoxyethyl group attached to the 2' hydroxyl and has the structure

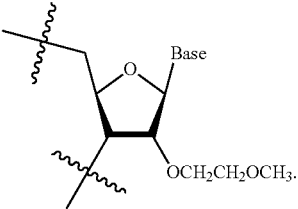

As used herein, a "locked nucleic acid" or "LNA" refers to a modified ribose sugar that includes a linkage that connects the 2'-position to the 4'-position of the 5-membered ring. Examples of locked nucleic acids include

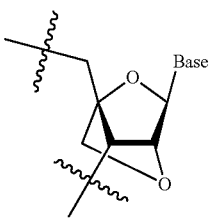

and

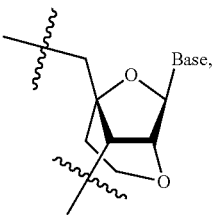

and those described in PCT publications WO 2011/052436, WO 2014/046212, and WO 2015/125783, each of which are hereby expressly incorporated by reference for the purpose of their disclosure of LNAs.

As used herein, "2'-O-Ethyl" refers to a modified ribose sugar that has an ethyl group attached to the 2' hydroxyl and has the structure

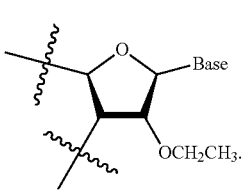

As used herein, "cEt" refers to a modified ribose sugar that includes a methyl that bridges the 2' hydroxyl and the 4' carbon, and has the structure

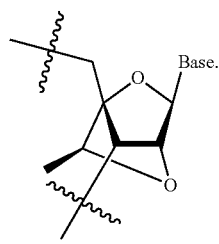

As used herein, "scpBNA" refers to a modified ribose sugar where a cyclopropane bridges the 2' hydroxyl and 4' carbon and has the structure

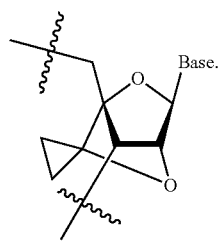

As used herein, "AmNA" refers to a modified ribose sugar where the 2' and 4' carbon are bridged with an amide bond and has the structure

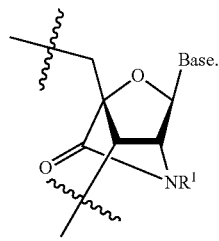

As used herein, an "unlocked nucleic acid" or "UNA" refers to a modified nucleotide wherein the bond between the 2'-position and the 3'-position of the 5-membered sugar ring is not present (acyclic ribose), and has the structure

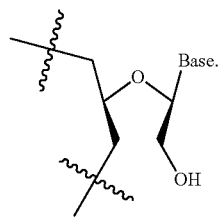

In each of the structures, the "Base", referring to a nucleobase, can be an unmodified base, a modified base or absent, such that the nucleotide is abasic. When not indicated, the nucleotide may be an unmodified nucleotide, modified nucleotide, or abasic.

A "modified base" refers to any base other than adenine, cytosine, guanine, thymine and uracil. For example, a modified base can be a substituted adenine, a substituted cytosine, a substituted 5-methylcytosine, a substituted guanine, a substituted thymine, or a substituted uracil. Alternatively, a modified base can make up a modified nucleoside such as a substituted cytidine, a substituted 5-methyl-cytidine, a substituted uridine, a substituted 5-methyluridine, a substituted guanosine, a substituted adenosine, a substituted deoxycytidine, a substituted 5-methyl-deoxycytidine, a substituted deoxyuridine, a substituted deoxyguanosine, a substituted deoxyadenosine, or a substituted thymidine.

When a specific linkage between the nucleotides are not specified, the linkage may be a phosphodiester or a non-phosphodiester linkage and may be a 3'-5' linkage and 2'-5' linkage, such as a phosphorothioate, a methylphosphonate, a phosphoramidate, a thiophosphoramidate, a phosphonoacetate, an amide linkage, or a boranophosphate linkage. The phosphodiester can have the structure

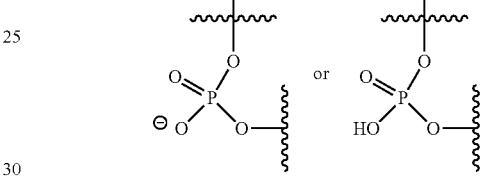

As used herein, a phosphorothioate is used as understood by those skilled in the art and refers to a phosphate wherein one oxygen is replaced with a sulfur. The phosphorothioate can have the structure

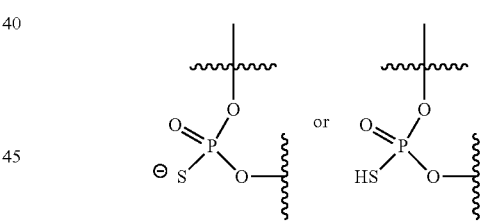

As used herein, a methylphosphonate is used as understood by those skilled in the art and refers to a phosphate wherein one oxygen is replaced with a methyl. The methylphosphonate can have the structure

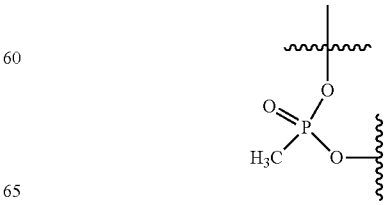

As used herein, a phosphoramidate is used as understood by those skilled in the art and refers to a phosphate wherein one oxygen is replaced with an amide. The phosphoramidate can have the structure

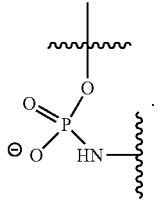 [SMILES: *NP(=O)([O-])O*]

As used herein, a thiophosphoramidate is used as understood by those skilled in the art and refers to a phosphate wherein one oxygen is replaced with a sulfur and one oxygen is replaced with an amide. The thiophosphoramidate can have the structure

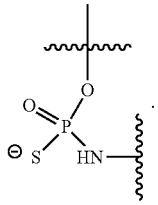 [SMILES: *NP(=O)([S-])O*]

As used herein, a phosphonoacetate is used as understood by those skilled in the art and refers to a phosphate wherein one oxygen is replaced with a —CH$_2$—C(=O)O$^-$ or —CH$_2$—C(=O)OH. The phosphonoacetate can have the structure

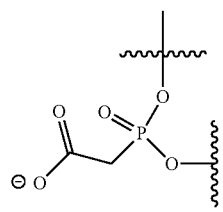 [SMILES: *OP(=O)(CC(=O)[O-])O*]

or

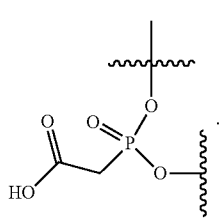 [SMILES: *OP(=O)(CC(=O)O)O*]

As used herein, an amide linkage is used as understood by those skilled in the art and refers to an amide. The amide linkage can have the structure

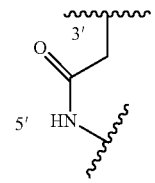

As used herein, a boranophosphate is used as understood by those skilled in the art and refers to a phosphate, wherein one oxygen is replace with a boron group. The boranophosphate can have the structure

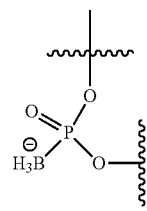

In some embodiments, the nucleosides are linked with all phosphodiester linkages. In some embodiments, the nucleosides are linked with all phosphorothioate linkages. In some embodiments, the nucleosides are linked with all methylphosphonate linkages. In some embodiments, the nucleosides are linked with all phosphoramidate linkages. In some embodiments, the nucleosides are linked with all thiophosphoramidate linkages. In some embodiments, the nucleosides are linked with all phosphonoacetate linkages. In some embodiments, the nucleosides are linked with all amide linkages. In some embodiments, the nucleosides are linked with all boranophosphate linkages. In some embodiments, the nucleosides are linked with a combination of phosphodiester and phosphorothioate linkages. In some embodiments, the nucleosides are linked with a combination of phosphodiester, phosphorothioate, methylphosphonate, phosphoramidate, thiophosphoramidate, phosphonoacetate, amide, and boranophosphate linkages, including combinations where at least one type of linkage is not present.

Those skilled in the art understand that when the linkage is a non-phosphodiester linkage, the phosphorus can be a chiral center. For example, in a phosphorothioate, the phosphorus can be a (R)-stereocenter or a (S)-stereocenter. In some embodiments, each phosphorus of a non-phosphodiester linkage can be a (R)-stereocenter. In other embodiments, each phosphorus of a non-phosphodiester linkage can be a (S)-stereocenter. For example, in an oligonucleotide that has a phosphorothioate between each nucleotide, each phosphorothioate can be in the (S)-configuration. In still other embodiments, the oligonucleotide can include at least one non-phosphodiester linkage, wherein the phosphorus can be a (S)-stereocenter, and at least one non-phosphodiester linkage, wherein the phosphorus can be a (R)-stereocenter. In some embodiments, a particular linkage within an oligonucleotide may be present in a racemic mixture. In some embodiments, a particular linkage within an oligonucleotide may be present in an unequal mixture of (R) and (S) stereoisomers. For example, a particular linkage may be present where the ratio between (R) and (S) stereoisomers is 0%:100%, 10%:90%, 20%:80%, 30%:70%, 40%:60%, 50%:50%, 60%:40%, 70%:30%, 80%:20%, 90%:10%, 100%:0%, or any ratio in the range defined between any two aforementioned ratios. In some embodiments, a particular linkage within an oligonucleotide is enantiomerically pure, (R) enantiomerically pure, or (S) enantiomerically pure.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. Likewise, it is understood that, in any compound described, all tautomeric forms are also intended to be included.

As used herein, the term "small interfering RNA" or "siRNA" has its ordinary meaning as understood in light of the specification, and refers to a class of double-stranded RNA molecules, which interferes with the expression of specific genes having a nucleotide sequence complementary to the siRNA. siRNAs typically have a well-defined structure: a short double-stranded RNA (dsRNA) with phosphorylated 5' ends and hydroxylated 3' ends with two overhanging nucleotides. The Dicer enzyme catalyzes production of siRNAs from long dsRNAs and small hairpin RNAs (shRNAs). Double stranded siRNA associates with the RNA-inducing silencing complex (RISC), one strand (the passenger, or sense strand) is lost, and the remaining strand (the guide strand, or antisense strand) cooperates with RIS to bind complementary target RNA. In some embodiments, the siRNA disclosed herein may include about 15 to about 35 base pairs, such as 15, 16, 17, 18, 19, 20, 21, 22, 23, 24, 25, 26, 27, 28, 29, 30, 31, 32, 33, 34, or 35 base pairs in length. In some embodiments, the siRNA antisense strand is complementary to a fragment or portion of target mRNA, such as CD274 mRNA, for initiating transcriptional silencing. In some embodiments, the siRNA provided herein includes a modification. In some embodiments, any of the modifications described herein are applied to the sense strand. In some embodiments, any of the modifications described herein are applied to the antisense strand. In some embodiments, the modification confers one or more beneficial characteristics to the siRNA, such as limiting degradation of the siRNA, improving half-life of the siRNA, increasing potency, activity, stability, safety, efficacy, solubility, permeability, selectivity, bioavailability, or melting temperature.

In some embodiments, the antisense strand of the siRNA includes a 5'-phosphate. In some embodiments, the antisense strand of the siRNA includes a 5'-phosphate mimic. The phosphate or phosphate mimic includes OC- and/or β-configuration with respect to the sugar ring or combinations thereof. The phosphate or phosphate mimics is a natural phosphate, phosphorothioate, phosphorodithioate, boranophosphate, boranothiophosphate, phosphonate, halogen substituted phosphonates, phosphoramidates, phosphodiester, phosphotriester, thiophosphodiester, thiophosphotriester, diphosphates, and/or triphosphates. Suitable phosphate mimics include 5'-phosphonates, such as 5'-methylenephosphonate (5'-MP) and 5'-(E)-vinylphosphonate (5'-VP), and 4'-phosphate analogs that are bound to the 4'-carbon of the sugar moiety (e.g., a ribose or deoxyribose or analog thereof) of the 5'-terminal nucleotide of an oligonucleotide, such as 4'-oxymethylphosphonate, 4'-thiomethylphosphonate, or 4'-aminomethylphosphonate. In some embodiments, the 5'-phosphate mimic is a 5'-vinylphosphonate.

The siRNA can be modified with at least one moiety, such as a targeting moiety. In some embodiments, the targeting moiety is a lipophilic moiety. In some embodiments, the targeting moiety is a long chain fatty acid having a general structure of $CH_3(CH_2)_n(CH)_mCOOH$, wherein n is a whole number ranging from 1 to 30, and wherein m is a whole number ranging from 1 to 30. Examples of a targeting moiety include, but are not limited to N-acetylgalactosamine (GalNAc, including, for example, a triantennary-GalNAc, including, for example, GalNAc3, GalNAc4, GalNAc5, GalNAc6 and/or GalNAc7), folic acid, cholesterol, tocopherol, vitamin E, or palmitate. Additional examples of long chain fatty acids include, but are not limited to, docohexanoic acid, docosanoic acid, linoleic acid (omega-6), linolenic acid (omega-3), oleic acid, octanoic acid, decanoyl acid, dodecanoyl acid, stearic acid, eicosanoic acid, and arachidonic acid. In some embodiments, the targeting moiety results in preferential targeting of the siRNA to a certain organ or tissue, such as the liver, heart, lung, brain, bone, muscle, kidney, stomach, small intestine, large intestine, or pancreas. In some embodiments, a targeting moiety is conjugated to the 5' end of the siRNA. In some embodiments, a targeting moiety is conjugated to the 5' phosphate of the siRNA. In some embodiments, a targeting moiety is conjugated to the 3' end of the siRNA. In some embodiments, a targeting moiety is conjugated to the 3' sugar hydroxyl of the siRNA. In some embodiments, a targeting moiety is conjugated to the 5' end and another targeting moiety is conjugated to the 3' end of the siRNA. In some embodiments, a second targeting moiety can be conjugated to a first targeting moiety. In some embodiments, a targeting moiety is attached with a linker. In some embodiments, the linker is a nucleotide, such as adenine, guanine, cytosine, thymine, or uracil nucleotides, or non-nucleoside linkers, including triethylene glycol (TEG), hexaethylene glycol (HEG), or alkyl amino linker.

GalNAc as used herein has the following structure

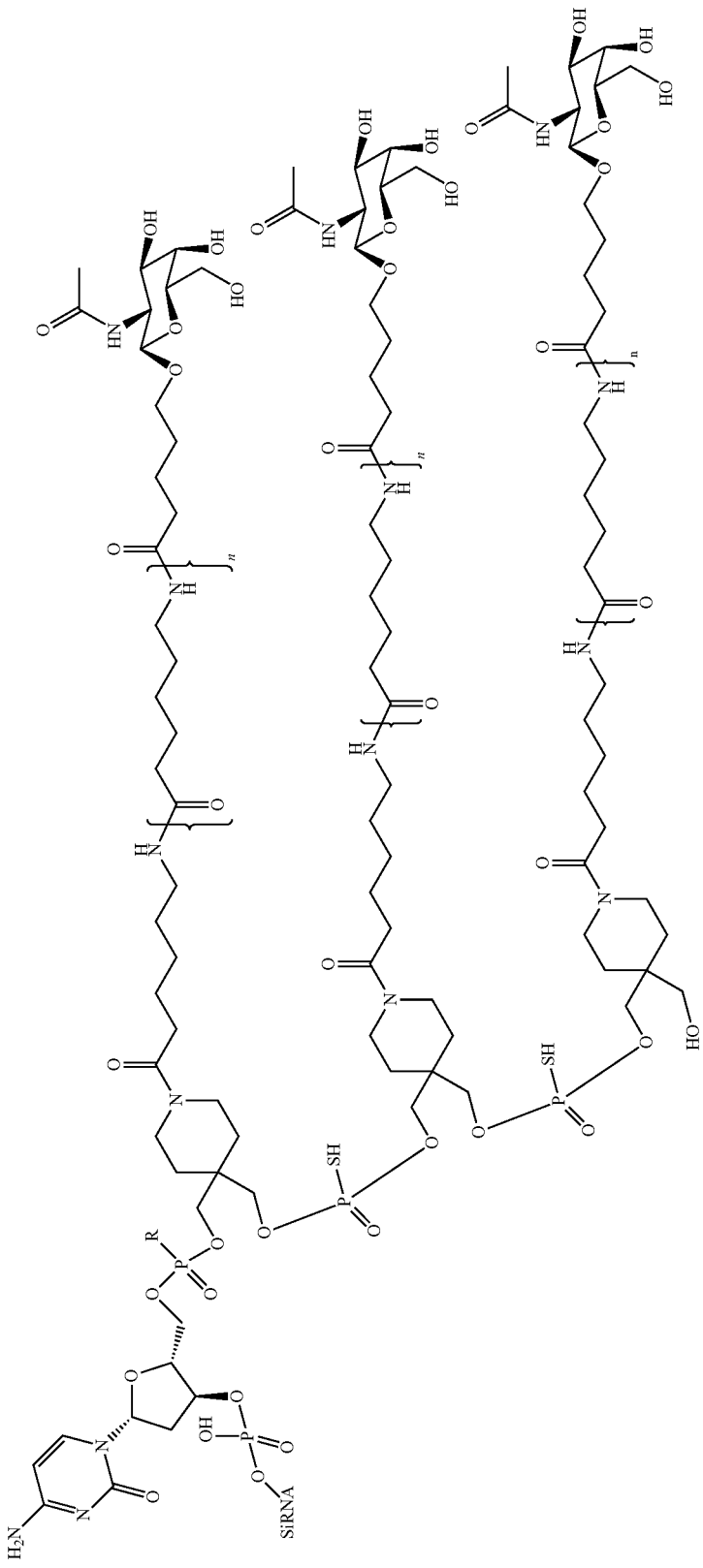

wherein R is OH or SH, and wherein n is any integer. In some embodiments, the deoxycytosine nucleotide shown in this structure linking the siRNA to the GalNAc moiety is optional, and can be omitted. In some embodiments, n ranges from 0 to 10, such as 0, 1, 2, 3, 4, 5, 6, 7, 8, 9, or 10. For example, for GalNAc4, n=1; and for GalNAc6, n=2. However, it is to be understood that n may equal any integer and may be selected based on the desired characteristic of the targeting moiety.

As used herein, the term "Xmer" refers to an oligonucleotide or nucleic acid polymer that is "X" nucleotides long. For example, a 14 mer is an oligonucleotide or nucleic acid polymer that is 14 nucleotides long, and a 20 mer is an oligonucleotide or nucleic acid polymer that is 20 nucleotides long. In some embodiments, the "X" refers to the total number of nucleotides. In other embodiments, the "X" refers to the number of nucleotides involved in binding to the target, while the oligonucleotide or nucleic acid polymer may have additional nucleotides or components that are not involved in binding to the target.

In some embodiments, at least one siRNA is used to treat liver disease. In some embodiments, the liver disease includes but is not limited to liver cancer, hepatocellular carcinoma (HCC), cholangiocarcinoma, hepatitis, hepatitis A, hepatitis B, hepatitis C, hepatitis D, or any combination thereof. In some embodiments, the at least one siRNA is used to silence expression of a gene involved in a liver disease. In some embodiments, the gene is CD274. In some embodiments, the at least one siRNA results in at least 10%, 20%, 30%, 40%, 50%, 60%, 70%, 80%, 90%, 91%, 92%, 93%, 94%, 95%, 96%, 97%, 98%, 99%, or 100% reduction in the disease or symptoms thereof, or in an amount within a range defined by any two of the aforementioned values.

The term "isolated" as used herein refers to material that is substantially or essentially free from components that normally accompany it in its native state. For example, an "isolated cell," as used herein, includes a cell that has been purified from the milieu or organisms in its naturally occurring state, a cell that has been removed from a subject or from a culture, for example, it is not significantly associated with in vivo or in vitro substances.

As used herein, the abbreviations for any protective groups and other compounds are used, unless indicated otherwise, in accord with their common usage.

It is to be understood that where compounds disclosed herein have unfilled valencies, then the valencies are to be filled with hydrogen or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

siRNA Synthesis

Each of 2'-OMe, 2'-MOE, and LNA phosphoramidite monomers were procured from commercially-available sources. All the monomers were dried in vacuum desiccator with desiccants ($P_2O_5$, RT 24 h). Universal solid supports (CPG) attached were obtained from ChemGenes. The chemicals and solvents for synthesis workflow were purchased from VWR/Sigma commercially-available sources and used without any purification or treatment. Solvent (Acetonitrile) and solutions (amidite and activator) were stored over molecular sieves during synthesis.

The control and target oligonucleotide sequences were synthesized on an Expedite 8909 synthesizer using the standard cycle written by the manufacturer with modifications as needed to wait steps and coupling steps. The solid support was controlled pore glass and the monomers contained standard protecting groups. Each chimeric oligonucleotide was individually synthesized using commercially available 5'-O-(4,4'-dimethoxytrityl)-3'-O-(2-cyanoethyl-N,N-diisopropyl) DNA, 2'-OMe, 2'-MOE and or LNA phosphoramidite monomers of 6-N-benzoyladenosine ($A^{Bz}$), 4-N-acetylcytidine ($C^{Ac}$), 2-N-isobutyrylguanosine ($G^{iBu}$), and Uridine (U) or Thymidine (T), according to standard solid phase phosphoramidite synthesis protocols. The 2'-O-Me-2,6, diaminopurine phosphoramidite was purchased from Glen Research. The phosphoramidites were prepared as 0.1 M solutions in anhydrous acetonitrile. 5-Ethylthio-tetrazole was used as activator, 3% Dichloroacetic acid in dichloromethane was used to detritylate, acetic anhydride in THF and 16% N-methylimidazole in THF were used to cap, and DDTT ((dimethylamino-methylidene) amino)-3H-1,2,4-dithiazaoline-3-thione was used as the sulfur-transfer agent for the synthesis of oligoribonucleotide phosphorothioates. An extended coupling of 0.1M solution of phosphoramidite in $CH_3CN$ in the presence of 5-(ethylthio)-1H-tetrazole activator to a solid bound oligonucleotide followed by extended capping, oxidation and deprotection to afford the modified oligonucleotides. The stepwise coupling efficiency of all modified phosphoramidites was more than 98.5%.

Deprotection and cleavage from the solid support was achieved with mixture of ammonia methylamine (1:1, AMA) for 15 min at 65° C., when the universal linker was used, the deprotection was left for 90 min at 65° C. or solid supports were heated with aqueous ammonia (28%) solution at 55° C. for 8 h to deprotect the base labile protecting groups. After filtering to remove the solid support, the deprotection solution was removed under vacuum in a GeneVac centrifugal evaporator. Tables 1-3 depicts exemplary structures of 2'-OMe, 2'-MOE, and LNA phosphoramidite monomers TABLE 1
2'-OMe Phosphoramidite Monomers
2'-OMe-A Phosphoramidite
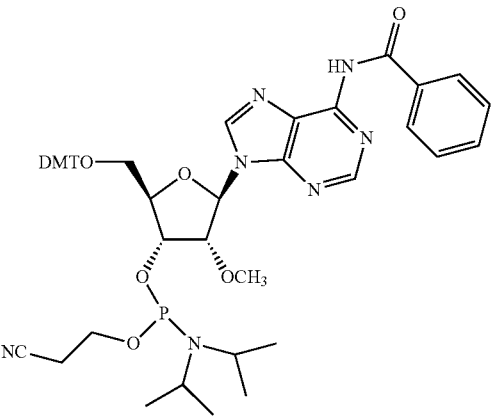
2'-OMe-C Phosphoramidite
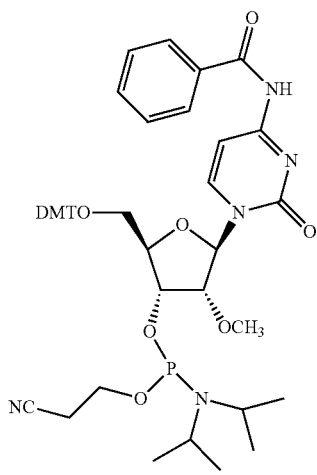
2'-OMe-G Phosphoramidite
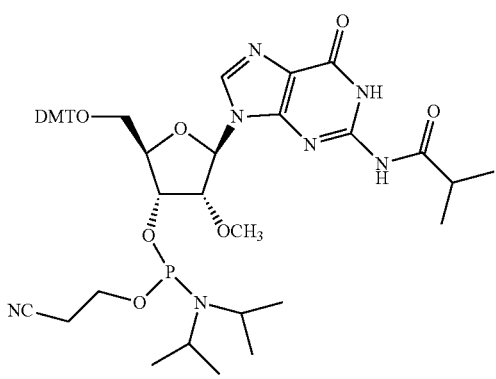

TABLE 1-continued
2'-OMe Phosphoramidite Monomers
2'-OMe-U Phosphoramidite
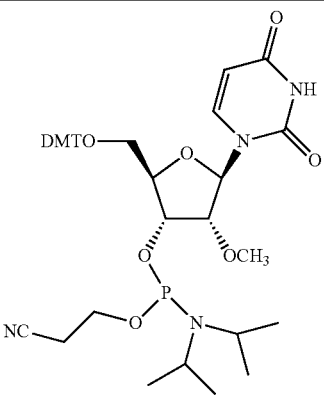
20
TABLE 2
2'-MOE Phosphoramidite Monomers
2'-MOE-A Phosphoramidite
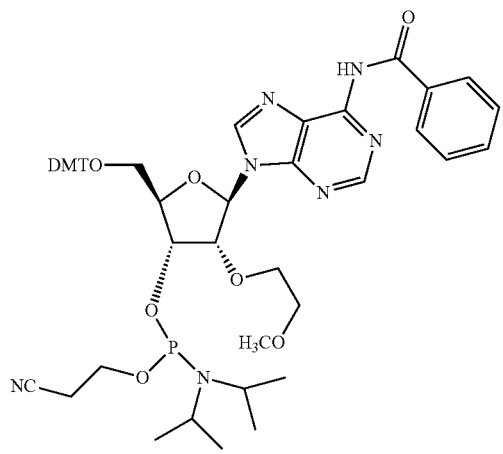
2'-MOE-(5m)C Phosphoramidite
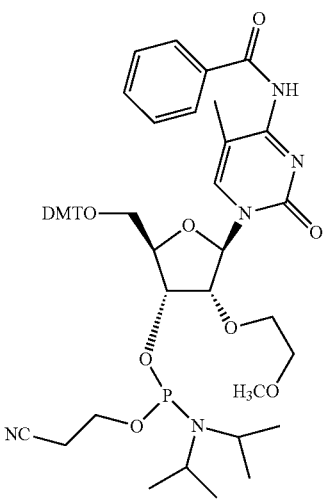

TABLE 2-continued
2'-MOE Phosphoramidite Monomers
2'-MOE-G Phosphoramidite
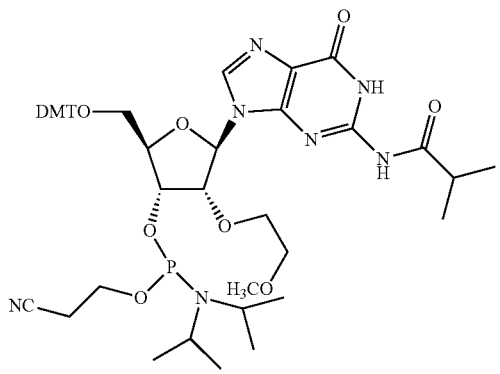
2'-MOE-T Phosphoramidite
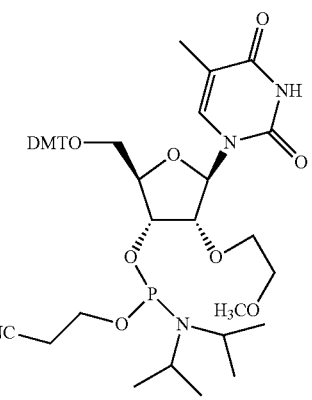
TABLE 3
2'-LNA Phosphoramidite Monomers
LNA-A Phosphoramidite
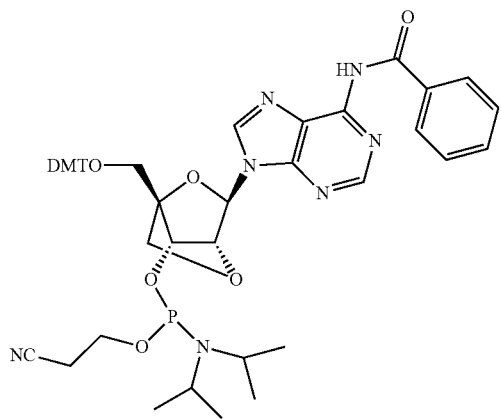

TABLE 3-continued

2'-LNA Phosphoramidite Monomers

LNA-(5m)C Phosphoramidite

LNA-G Phosphoramidite

LNA-T Phosphoramidite

The AmNA and Scp-BNA phosphoramidite monomers of 6-N-benzoyladenosine ($A^{Bz}$), 4-N-acetylcytidine ($C^{Ac}$), 2-N-isobutyrylguanosine ($G^{iBu}$), and Thymidine (T) received from LUXNA Technologies. All the monomers were dried in a vacuum desiccator with desiccants ($P_2O_5$, at room temperature for 24 hours). For the AmNA-PS-DNA-PS and scp-BNA-PS-DNA-PS modifications, the synthesis was carried out on a 1 µM scale in a 3' to 5' direction with the phosphoramidite monomers diluted to a concentration of 0.12 M in anhydrous $CH_3CN$ in the presence of 0.3 M 5-(benzylthio)-1H-tetrazole activator (coupling time 16-20 min) to a solid bound oligonucleotide followed by modified capping, oxidation and deprotection to afford the modified oligonucleotides. The stepwise coupling efficiency of all modified phosphoramidites was more than 97%. The DDTT (dimethylamino-methylidene) amino)-3H-1, 2, 4-dithiazaoline-3-thione was used as the sulfur-transfer agent for the synthesis of the oligoribonucleotide phosphorothioates. Oligonucleotide-bearing solid supports were washed with 20% DEA solution in acetonitrile for 15 min then the column was washed thoroughly with AcCN. The support was heated at 65° C. with Diisopropylamine:water:Methanol (1:1:2) for 5 h in heat block to cleave from the support and deprotect the base labile protecting groups. Tables 4 and 5 depicts exemplary structures of the AmNA and Scp-BNA phosphoramidite monomers.

TABLE 4
am-NCH₃ Phosphoramidite Monomers
am-NCH₃-A phosphoramidite
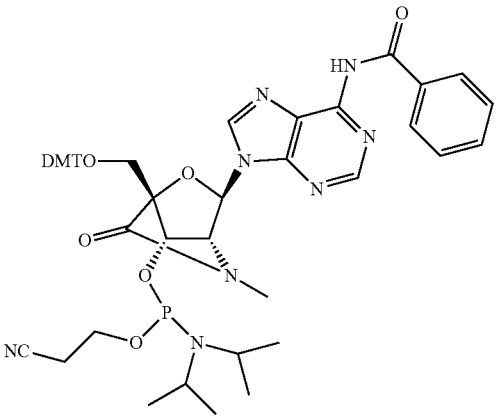
am-NCH₃-(5m)C phosphoramidite
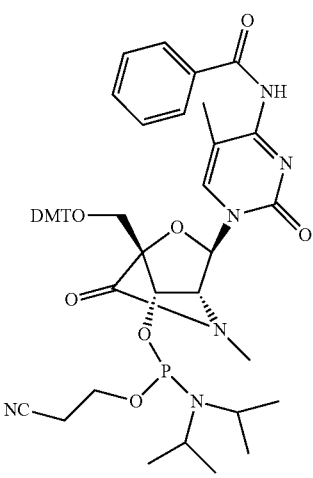
am-NCH₃-G Phosphoramidite
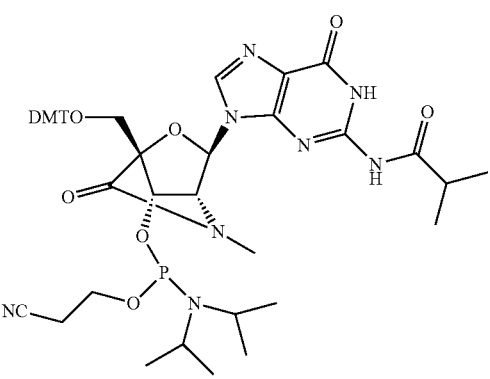

TABLE 4-continued
am-NCH₃ Phosphoramidite Monomers
am-NCH₃-T Phosphoramidite
20
TABLE 5
Scp-BNA Phosphoramidite Monomers
Scp-BNA-A phosphoramidite
Scp-BNA-(5m)C phosphoramidite
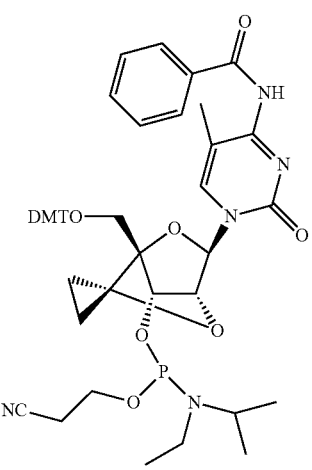

TABLE 5-continued

Scp-BNA Phosphoramidite Monomers

Scp-BNA-G Phosphoramidite

Scp-BNA-T Phosphoramidite

The cholesterol, tocopherol phosphoramidite, and solid supports were received from ChemGenes. The cholesterol and Tocopherol conjugated oligonucleotides were obtained by initiating solid phase synthesis on cholesterol and Tocopherol supports attached on TEG linker for 3'-conjugation while final coupling of the phosphoramidite provided the 5'-conjugated oligonucleotides.

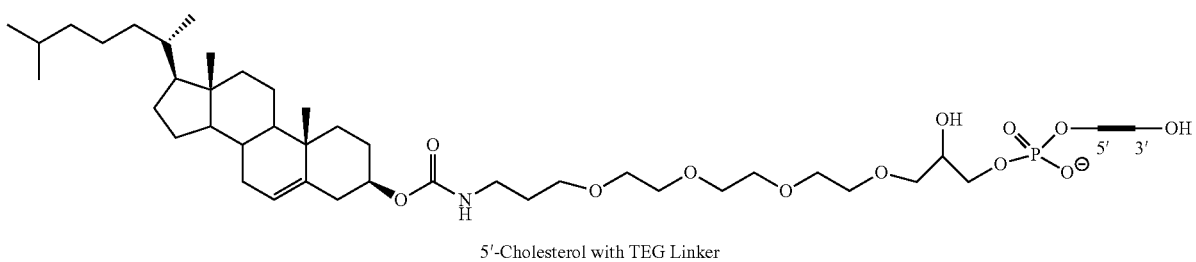

5'-Cholesterol with TEG Linker

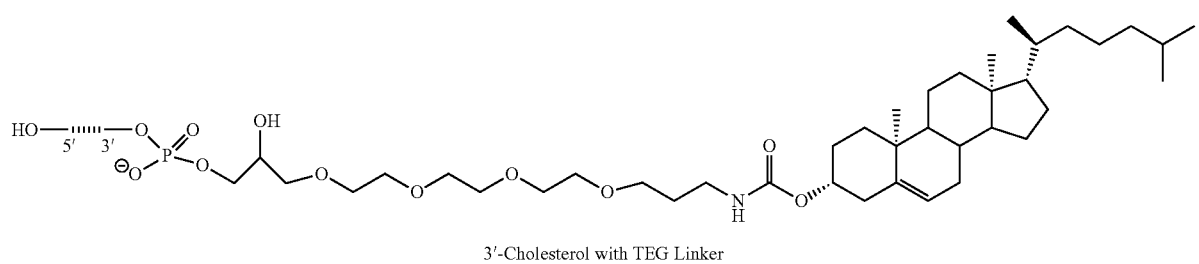

3'-Cholesterol with TEG Linker

-continued

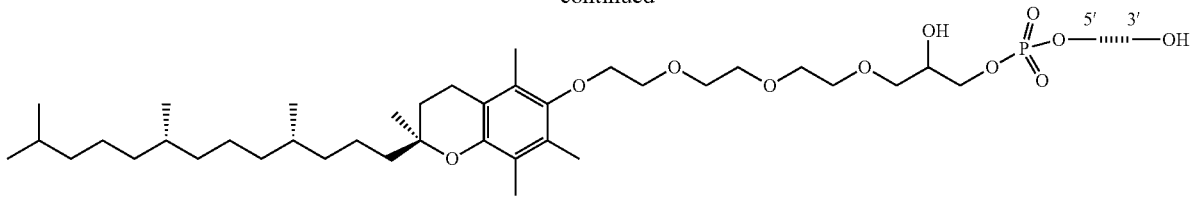

5′-tocopherol-TEG linker

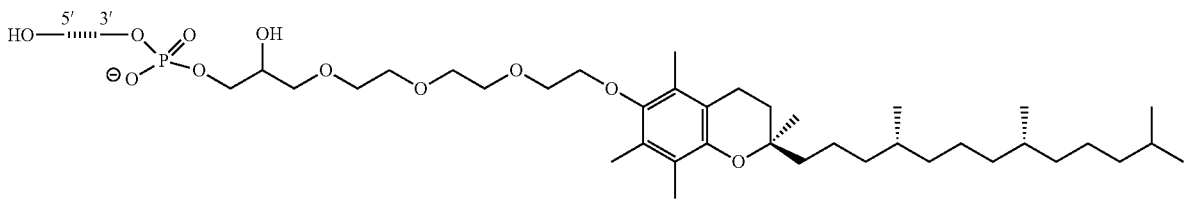

3′-tocopherol-TEG linker

Quantitation of Crude Oligomer or Raw Analysis

Samples were dissolved in deionized water (1.0 mL) and quantified as follows: Blanking was first performed with water alone (1.0 mL), then 20 µL of sample and 980 µL of water were mixed well in a microfuge tube, transferred to cuvette and absorbance reading obtained at 260 nm. The crude material was dried and stored at −20° C.

Crude HPLC/LC-MS Analysis

The 0.1 OD of the crude samples were used for crude MS analysis. After confirming the crude LC-MS data, the purification step was performed.

HPLC Purification

The Phosphodiester (PO), Phosphorothioate (PS) and chimeric modified oligonucleotides were purified by anion-exchange HPLC. The buffers were 20 mM sodium phosphate in 10% $CH_3CN$, pH 8.5 (buffer A) and 20 mM sodium phosphate in 10% $CH_3CN$, 1.8 M NaBr, pH 8.5 (buffer B). Fractions containing full-length oligonucleotides were pooled, desalted and lyophilized.

The conjugated oligonucleotides were purified by an in-house packed RPC-Source15 reverse-phase column. The buffers were 20 mM sodium acetate in 10% $CH_3CN$, (buffer A) and $CH_3CN$ (buffer B). Fractions containing full-length oligonucleotides were pooled, desalted and lyophilized.

Desalting of Purified Oligomer

The purified dry oligomer was then desalted using Sephadex G-25 M (Amersham Biosciences). The cartridge was conditioned with 10 mL of deionized water thrice. The purified oligonucleotide dissolved thoroughly in 2.5 mL deionized water was applied to the cartridge with very slow drop wise elution. The salt free oligomer was eluted with 3.5 mL deionized water directly into a screw cap vial.

Final HPLC and Electrospray LC/MS Analysis

Approximately 0.10 OD of oligomer is dissolved in water and then pipetted in special vials for IEX-HPLC and LC/MS analysis. Analytical HPLC and ES LC-MS established the integrity of the chimeric oligonucleotides.

The cholesterol and tocopherol conjugated sequences were analyzed by high-performance liquid chromatography (HPLC) on a Luna C8 reverse-phase column. The buffers were 20 mM NaOAc in 10% $CH_3CN$ (buffer A) and 20 mM NaOAc in 70% $CH_3CN$ (buffer B). Analytical HPLC and ES LC-MS established the integrity of the conjugated oligonucleotides Post Synthesis Conjugation:

5′-Folate conjugated siRNAs: To a solution of 5′-hexylamino siRNA in 0.1 M sodium tetraborate buffer, pH 8.5 (2 mM) a solution of Folate-NHS ester (3 mole equivalent) dissolved in DMSO (40 mM) was added, and the reaction mixture was stirred at room temperature for 3 h. The Reaction mixture concentrated under reduced pressure. The residue was dissolved in water and purified by HPLC on a strong anion exchange column (GE Healthcare Bioscience, Source 30Q, 30 µm, 2.54×8 cm, A=100 mM ammonium acetate in 30% aqueous $CH_3CN$, B=1.8 M NaBr in A, 0-60% of B in 60 min, flow 10 mL/min). The residue was desalted by in house packed Sephadex G-25 column to yield the 5′-Folate conjugated siRNAs in an isolated yield of 62-80%. The folate conjugated siRNAs were characterized by IEX-HPLC and Thermo Fischer ESI-LC-MS system. Table 6 depicts exemplary nucleic acids and structures.

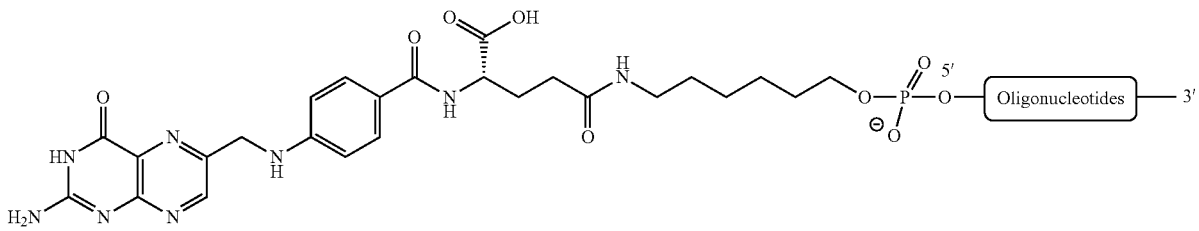

TABLE 6

Abbreviations for nucleic acid structures

| Abbreviation | Name | Structure |
|---|---|---|
| A | Adenine | (adenine structure) |
| G | Guanine | (guanine structure) |
| C | Cytosine | (cytosine structure) |
| U | Uracil | (uracil structure) |
| T | Thymine | (thymine structure) |
| (5m)C | 5-methyl-cytosine | (5-methyl-cytosine structure) |
| DAP | 2,6-diaminopurine | (2,6-diaminopurine structure) |

TABLE 6-continued

Abbreviations for nucleic acid structures

| Abbreviation | Name | Structure |
|---|---|---|
| d | Deoxy | (deoxyribose-Base structure) |
| ps | Phosphorothioate | (phosphorothioate structure, two tautomers) |
| ln | LNA | (LNA structure with Base) |
| am | AmNA | (AmNA structure with Base and NH) |
| scp | Scp-BNA | (Scp-BNA structure with Base) |
| m | 2'-OMe | (2'-OMe ribose-Base structure with OCH$_3$) |

TABLE 6-continued

Abbreviations for nucleic acid structures

| Abbreviation | Name | Structure |
|---|---|---|
| moe | 2'-MOE | (structure with Base, O, OCH$_2$CH$_2$OCH$_3$) |
| cet | cEt | (structure with Base, O, O) |
| gn | GNA | (structure with Base, O) |

Any of the structures shown in Table 6 can be combined with any base, thereby generating various combinations of structures. For example, using the abbreviations and structures from Table 6, one skilled in the art understands that the abbreviation "AmG" represents

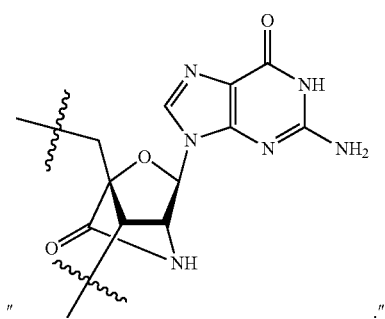

Furthermore, additional structures not depicted in the tables, but described elsewhere throughout the application may be used and combined with any base described in the tables or elsewhere throughout the application.

Pharmaceutical Compositions

Some embodiments described herein relate to pharmaceutical compositions that comprise, consist essentially of, or consist of an effective amount of an siRNA described herein and a pharmaceutically acceptable carrier, excipient, or combination thereof. A pharmaceutical composition described herein is suitable for human and/or veterinary applications.

The terms "function" and "functional" as used herein refer to a biological, enzymatic, or therapeutic function.

The terms "effective amount" or "effective dose" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "pharmaceutically acceptable salts" includes relatively non-toxic, inorganic and organic acid, or base addition salts of compositions, including without limitation, analgesic agents, therapeutic agents, other materials, and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc, and the like. Salts may also be formed with suitable organic bases, including those that are non-toxic and strong enough to form such salts. For example, the class of such organic bases may include but are not limited to mono-, di-, and trialkylamines, including methylamine, dimethylamine, and triethylamine; mono-, di-, or trihydroxyalkylamines including mono-, di-, and triethanolamine; amino acids, including glycine, arginine and lysine; guanidine; N-methylglucosamine; N-methylglucamine; L-glutamine; N-methylpiperazine; morpholine; ethylenediamine; N-benzylphenethylamine; trihydroxymethyl aminoethane.

"Formulation", "pharmaceutical composition", and "composition" as used interchangeably herein are equivalent terms referring to a composition of matter for administration to a subject.

The term "pharmaceutically acceptable" means compatible with the treatment of a subject, and in particular, a human.

The terms "agent" refers to an active agent that has biological activity and may be used in a therapy. Also, an "agent" can be synonymous with "at least one agent," "compound," or "at least one compound," and can refer to any form of the agent, such as a derivative, analog, salt or a prodrug thereof. The agent can be present in various forms, components of molecular complexes, and pharmaceutically acceptable salts (e.g., hydrochlorides, hydrobromides, sulfates, phosphates, nitrates, borates, acetates, maleates, tartrates, and salicylates). The term "agent" can also refer to any pharmaceutical molecules or compounds, therapeutic molecules or compounds, matrix forming molecules or compounds, polymers, synthetic molecules and compounds, natural molecules and compounds, and any combination thereof.

The term "subject" as used herein has its ordinary meaning as understood in light of the specification and refers to an animal that is the object of treatment, inhibition, or amelioration, observation or experiment. "Animal" has its ordinary meaning as understood in light of the specification and includes cold- and warm-blooded vertebrates and/or invertebrates such as fish, shellfish, or reptiles and, in particular, mammals. "Mammal" has its ordinary meaning as understood in light of the specification, and includes but is not limited to mice, rats, rabbits, guinea pigs, dogs, cats, sheep, goats, cows, horses, primates, such as humans, monkeys, chimpanzees, or apes. In some embodiments, the subject is human.

Proper formulation is dependent upon the route of administration chosen. Techniques for formulation and administration of the compounds described herein are known to those skilled in the art. Multiple techniques of administering a compound exist in the art including, but not limited to, enteral, oral, rectal, topical, sublingual, buccal, intraaural, epidural, epicutaneous, aerosol, parenteral delivery, including intramuscular, subcutaneous, intra-arterial, intravenous, intraportal, intra-articular, intradermal, peritoneal, intramedullary injections, intrathecal, direct intraventricular, intraperitoneal, intranasal or intraocular injections. Pharmaceutical compositions will generally be tailored to the specific intended route of administration. Pharmaceutical compositions can also be administered to isolated cells from a patient or individual, such as T cells, Natural Killer cells, B cells, macrophages, lymphocytes, stem cells, bone marrow cells, or hematopoietic stem cells.

The pharmaceutical compound can also be administered in a local rather than systemic manner, for example, via injection of the compound directly into an organ, tissue, cancer, tumor or infected area, often in a depot or sustained release formulation. Furthermore, one may administer the compound in a targeted drug delivery system, for example, in a liposome coated with a tissue specific antibody. The liposomes may be targeted to and taken up selectively by the organ, tissue, cancer, tumor, or infected area.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

As used herein, a "carrier" refers to a compound, particle, solid, semi-solid, liquid, or diluent that facilitates the passage, delivery and/or incorporation of a compound to cells, tissues and/or bodily organs. For example, without limitation, a lipid nanoparticle (LNP) is a type of carrier that can encapsulate an oligonucleotide to thereby protect the oligonucleotide from degradation during passage through the bloodstream and/or to facilitate delivery to a desired organ, such as to the liver.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "excipient" has its ordinary meaning as understood in light of the specification, and refers to inert substances, compounds, or materials added to a pharmaceutical composition to provide, without limitation, bulk, consistency, stability, binding ability, lubrication, disintegrating ability etc., to the composition. Excipients with desirable properties include but are not limited to preservatives, adjuvants, stabilizers, solvents, buffers, diluents, solubilizing agents, detergents, surfactants, chelating agents, antioxidants, alcohols, ketones, aldehydes, ethylenediaminetetraacetic acid (EDTA), citric acid, salts, sodium chloride, sodium bicarbonate, sodium phosphate, sodium borate, sodium citrate, potassium chloride, potassium phosphate, magnesium sulfate sugars, dextrose, fructose, mannose, lactose, galactose, sucrose, sorbitol, cellulose, serum, amino acids, polysorbate 20, polysorbate 80, sodium deoxycholate, sodium taurodeoxycholate, magnesium stearate, octylphenol ethoxylate, benzethonium chloride, thimerosal, gelatin, esters, ethers, 2-phenoxyethanol, urea, or vitamins, or any combination thereof. The amount of the excipient may be found in a pharmaceutical composition at a percentage of 0%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 95%, 100% w/w or any percentage by weight in a range defined by any two of the aforementioned numbers.

The term "adjuvant" as used herein refers to a substance, compound, or material that stimulates the immune response and increase the efficacy of protective immunity and is administered in conjunction with an immunogenic antigen, epitope, or composition. Adjuvants serve to improve immune responses by enabling a continual release of antigen, up-regulation of cytokines and chemokines, cellular recruitment at the site of administration, increased antigen uptake and presentation in antigen presenting cells, or activation of antigen presenting cells and inflammasomes. Commonly used adjuvants include but are not limited to alum, aluminum salts, aluminum sulfate, aluminum hydroxide, aluminum phosphate, calcium phosphate hydroxide, potassium aluminum sulfate, oils, mineral oil, paraffin oil, oil-in-water emulsions, detergents, MF59®, squalene, AS03, α-tocopherol, polysorbate 80, ASO4, monophosphoryl lipid A, virosomes, nucleic acids, polyinosinic:polycytidylic acid, saponins, QS-21, proteins, flagellin, cytokines, chemokines, IL-1, IL-2, IL-12, IL-15, IL-21, imidazoquinolines, CpG oligonucleotides, lipids, phospholipids, dioleoyl phosphatidylcholine (DOPC), trehalose dimycolate, peptidoglycans, bacterial extracts, lipopolysaccharides, or Freund's Adjuvant, or any combination thereof.

The term "purity" of any given substance, compound, or material as used herein refers to the actual abundance of the substance, compound, or material relative to the expected abundance. For example, the substance, compound, or material may be at least 80, 85, 90, 91, 92, 93, 94, 95, 96, 97, 98, 99, or 100% pure, including all decimals in between. Purity may be affected by unwanted impurities, including but not limited to side products, isomers, enantiomers, degradation products, solvent, carrier, vehicle, or contaminants, or any combination thereof. Purity can be measured technologies including but not limited to chromatography, liquid chromatography, gas chromatography, spectroscopy, LTV-visible spectrometry, infrared spectrometry, mass spectrometry, nuclear magnetic resonance, gravimetry, or titration, or any combination thereof.

Methods of Use

Some embodiments disclosed herein related to selecting a subject or patient in need. In some embodiments, a patient is selected who is in need of treatment, inhibition, amelioration, prevention or slowing of diseases or conditions associated with PD-L1 dysregulation. In some embodiments, such diseases or conditions associated with PD-L1 dysregulation may include, for example, cancer, HCC, viral infections, or HBV. In some embodiments, a patient is selected who has previously been treated for the disease or disorder described herein. In some embodiments, a patient is selected who has previously been treated for being at risk for the disease or disorder described herein. In some embodiments, a patient is selected who has developed a recurrence of the disease or disorder described herein. In some embodiments, a patient is selected who has developed resistance to therapies for the disease or disorder described herein. In some embodiments, a patient is selected who may have any combination of the aforementioned selection criteria.

siRNA molecules and pharmaceutical compositions comprising siRNA molecules disclosed herein can be evaluated for efficacy and toxicity using known methods. A non-limiting list of potential advantages of an siRNA described herein include improved stability, increased safety profile, increased efficacy, increased binding to the target, increased specificity for the target (for example, a cancer cell or virally infected cell).

The terms "treating," "treatment," "therapeutic," or "therapy" as used herein has its ordinary meaning as understood in light of the specification, and do not necessarily mean total cure or abolition of the disease or condition. The term "treating" or "treatment" as used herein (and as well understood in the art) also means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the patient. The length of the treatment period depends on a variety of factors, such as the severity of the condition, the age and genetic profile of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required.

Some embodiments described herein relate to a method of treating, inhibiting, ameliorating, preventing, or slowing the disease or disorder described herein. In some embodiments, the methods include administering to a subject identified as suffering from the disease or disorder described herein an effective amount of an siRNA described herein, or a pharmaceutical composition that includes an effective amount of an siRNA as described herein. Other embodiments described herein relate to using an siRNA as described herein in the manufacture of a medicament for treating, inhibiting, ameliorating, preventing, or slowing the disease or disorder described herein. Still other embodiments described herein relate to the use of an siRNA as described herein or a pharmaceutical composition that includes an effective amount of an siRNA as described herein for treating, inhibiting ameliorating, preventing, or slowing the disease or disorder described herein.

Some embodiments described herein relate to a method for inhibiting replication of a cancer cell or a virus that can include contacting the cell or virus or administering to a subject identified as suffering from a cancer or a viral infection with an effective amount of an siRNA described herein, or a pharmaceutical composition that includes an effective amount of an siRNA described herein. Other embodiments described herein relate to the use of an effective amount of an siRNA described herein, or a pharmaceutical composition that includes an effective amount of an siRNA described herein in the manufacture of a medicament for inhibiting replication of a cancer cell or virus. Still other embodiments described herein relate to an effective amount of an siRNA described herein, or a pharmaceutical composition that includes an effective amount of an siRNA described herein for inhibiting replication of a cancer cell or virus. In some embodiments, the cancer cell is an HCC cell. In some embodiments, the virus is hepatitis B.

Some embodiments described herein relate to a method for inhibiting cell proliferation, such as inhibiting cell proliferation of a cancer cell or cell infected with a virus, that can include administering to a subject identified as suffering from a disease wherein inhibiting cell proliferation is desirable with an effective amount of an siRNA described herein, or a pharmaceutical composition that includes effective amount of an siRNA described herein. Other embodiments described herein relate to the use of an effective amount of an oligonucleotide described herein, or a pharmaceutical composition that includes an effective amount of an siRNA described herein in the manufacture of a medicament for inhibiting cell proliferation, such as inhibiting cell proliferation of a cancer cell or cell infected with a virus. Still other embodiments described herein relate to an effective amount of an siRNA described herein, or a pharmaceutical composition that includes an effective amount of an siRNA described herein for inhibiting cell proliferation, such as inhibiting cell proliferation of a cancer cell or cell infected with a virus. In some embodiments, the cancer cell is an HCC cell. In some embodiments, the cell infected with a virus is infected with hepatitis B virus.

Some embodiments described herein relate to a method of inducing apoptosis of a cell (for example, a cancer cell or cell infected with a virus) that can include contacting the cell with an effective amount of an siRNA described herein, or a pharmaceutical composition that includes an effective amount of an siRNA as described herein. Other embodiments described herein relate to using an effective amount of an siRNA as described herein or a pharmaceutical composition that includes an effective amount of an siRNA in the manufacture of a medicament for inducing apoptosis of a cell, such as a cancer cell or cell infected with a virus. Still other embodiments described herein relate to the use of an effective amount of an siRNA as described herein or a pharmaceutical composition that includes an effective amount of an siRNA as described herein for inducing apoptosis of a cell, such as a cancer cell or cell infected with a virus. In some embodiments, the cancer cell is an HCC cell. In some embodiments, the cell infected with a virus is infected with hepatitis B virus.

Some embodiments described herein relate to a method of decreasing the viability of a cell (for example, a cancer cell or cell infected with a virus) that can include contacting the cell with an effective amount of an siRNA described herein, or a pharmaceutical composition that includes an effective amount of an siRNA as described herein. Other embodiments described herein relate to using an siRNA as described herein in the manufacture of a medicament for decreasing the viability of a cell, such as a cancer cell or cell infected with a virus. Still other embodiments described herein relate to the use of an effective amount of an siRNA as described herein or a pharmaceutical composition that includes an effective amount of an siRNA as described herein for decreasing the viability of a cell, such as a cancer cell or cell infected with a virus. In some embodiments, the cancer cell is an HCC cell. In some embodiments, the cell infected with a virus is infected with hepatitis B virus.

In some embodiments, the effective amount of an siRNA for a human subject is 1, 10, 50, 100, 200, 300, 400, 500, 600, 700, 800, 900, 1000 µg, or 1, 10, 20, 30, 40, 50, 60, 70, 80, 90, 100, 110, 120, 130, 140, 150, 160, 170, 180, 190, 200, 300, 400, 500, 600, 700, 800, 900, 1000 mg or any amount within the range defined by any two aforementioned amounts. In some embodiments, the effective amount of an siRNA for a human subject is 1, 10, 50, 100, 200, 300, 400, 500, 600, 700, 800, 900, 1000 ng/kg, or 1, 10, 20, 30, 40, 50, 60, 70, 80, 90, 100, 110, 120, 130, 140, 150, 160, 170, 180, 190, 200, 300, 400, 500, 600, 700, 800, 900, 1000 µg/kg or any amount within the range defined by any two aforementioned amounts. In some embodiments, the effective amount of an siRNA is dosed more than one time. In some embodiments, the siRNA dose is administered every 1, 2, 3, 4, 5, 6, 7 days, or 1, 2, 3, 4 weeks, or 1, 2, 3, 4, 5, 6, 7, 8, 9, 10, 11, 12 months, or 1, 2, 3, 4, 5 years, or any period or combination thereof within the range defined by any two aforementioned times. In some embodiments, at least one loading dose and at least one maintenance dose is administered to the subject, where the at least one loading dose is a higher dose of the siRNA than the at least one maintenance dose.

As used herein, the term "combination therapy" is intended to define therapies which comprise the use of a combination of two or more pharmaceutical compounds/agents or therapies. Thus, references to "combination therapy", "combinations" and the use of compounds/agents "in combination" in this application may refer to compounds/agents that are administered as part of the same overall treatment regimen. As such, the dosage or timing of each of the two or more compounds/agents may differ: each may be administered at the same time or at different times. Accordingly, the compounds/agents of the combination may be administered sequentially (e.g. before or after) or simultaneously, either in the same pharmaceutical formulation (i.e. together), or in different pharmaceutical formulations (i.e. separately). Each of the two or more compounds/agents in a combination therapy may also differ with respect to the route of administration.

The term "inhibitor", as used herein, refers to an enzyme inhibitor or receptor inhibitor which is a molecule that binds to an enzyme or receptor, and decreases and/or blocks its activity. The term may relate to a reversible or an irreversible inhibitor.

Cancer may be treated with surgery, radiation therapy, chemotherapy, targeted therapies, immunotherapy or hormonal therapies. Any of these mentioned therapies may be used in conjunction with another therapy as a combination therapy. Chemotherapeutic compounds include but are not limited to alemtuzumab, altretamine, azacitidine, bendamustine, bleomycin, bortezomib, busulfan, cabazitaxel, capecitabine, carboplatin, carmofur, carmustine, chlorambucil, chlormethine, cisplatin, cladribine, clofarabine, cyclophosphamide, cytarabine, dacarbazine, dactinomycin, daunorubicin, decitabine, denosumab, docetaxel, doxorubicin, epirubicin, estramustine, etoposide, everolimus, floxuridine, fludarabine, fluorouracil, fotemustine, gemcitabine, gemtuzumab, hydroxycarbamide, ibritumomab, idarubicin, ifosfamide, irinotecan, ixabepilone, lomustine, melphalan, mercaptopurine, methotrexate, mitomycin, mitoxantrone, nedaplatin, nelarabine, ofatumumab, oxaliplatin, paclitaxel, pemetrexed, pentostatin, pertuzumab, procarbazine, raltitrexed, streptozotocin, tegafur, temozolomide, temsirolimus, teniposide, tioguanine, topotecan, tositumomab, valrubicin, vinblastine, vincristine, vindesine, vinflunine, or vinorelbine, or any combination thereof.

As used herein, the term "protein kinase inhibitor" refers to inhibitors of protein kinases, serine/threonine kinases, tyrosine kinases, or dual-specificity kinases for the treatment of cancer or other illness. In some embodiments, the protein kinase inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the protein kinase inhibitor includes but is not limited to acalabrutinib, adavosertib, afatinib, alectinib, axitinib, binimetinib, bosutinib, brigatinib, cediranib, ceritinib, cetuximab, cobimetinib, crizotinib, cabozantinib, dacomitinib, dasatinib, entrectinib, erdafitinib, erlotinib, fostamatinib, gefitinib, ibrutinib, imatinib, lapatinib, lenvatinib, lestaurtinib, lortatinib, masitinib, momelotinib, mubritinib, neratinib, nilotinib, nintedanib, olmutinib, osimertinib, pacritinib, panitumumab, pazopanib, pegaptanib, ponatinib, radotinib, regorafenib, rociletinib, ruxolitinib, selumetinib, semaxanib, sorafenib, sunitinib, SU6656, tivozanib, toceranib, trametinib, trastuzumab, vandetanib, or vemurafenib, or any combination thereof.

As used herein, the term "checkpoint inhibitor" refers to an immunotherapy that targets immune checkpoints to stimulate immune function. In some embodiments, the checkpoint inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the immune checkpoint is the PD-1/PD-L1 checkpoint. In some embodiments, the PD-1 checkpoint includes but is not limited to nivolumab, pembrolizumab, spartalizumab, cemiplimab, camrelizumab, sintilimab, tislelizumab, toripalimab, AMP-224 or AMP-514, or any combination thereof. In some embodiments, the PD-L1 checkpoint inhibitor includes but is not limited to atezolizumab, avelumab, durvalumab, KN035, AUNP12, CA-170, or BMS-986189, or any combination thereof. In some embodiments, the immune checkpoint is the CTLA-4 checkpoint. In some embodiments, the CTLA-4 checkpoint inhibitor includes but is not limited to ipilimumab or tremilimumab, or any combination thereof.

As used herein, the term "VEGF inhibitor" refers to inhibitors of vascular endothelial growth factor (VEGF) or a VEGF receptor (VEGFR). In some embodiments, the VEGF inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the VEGF inhibitor includes but is not limited to aflibercept, axitinib, bevacizumab, brivanib, cabozantinib, cediranib, lenvatinib, linifinib, nintedanib, pazopanib, ponatinib, ramucirumab, regorafenib, semaxanib, sorafenib, sunitinib, tivozanib, toceranib, or vandetanib, or any combination thereof.

As used herein, the term "antiviral medication" refers to a pharmaceutical composition administered to treat a viral infection. In some embodiments, the viral infection is caused by adenovirus, Ebola virus, coronavirus, Epstein-Barr virus (EBV), Friend virus, hantavirus, hepatitis B virus (HBV), hepatitis C virus (HCV), herpes simplex virus, human immunodeficiency virus (HIV), human metapneumovirus, human papillomavirus (HPV), influenza virus, Japanese encephalitis virus, Kaposi's sarcoma-associated herpesvirus, lymphocytic choriomeningitis virus, parainfluenza virus, rabies virus, respiratory syncytial virus, rhinovirus, varicella zoster virus. In some embodiments, the antiviral medication is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the antiviral medication is an interferon, a capsid assembly modulator, a sequence specific oligonucleotide, an entry inhibitor, or a small molecule immunomodulatory. In some embodiments, the antiviral medication includes but is not limited to AB-423, AB-506, ABI-H2158, ABI-HO731, acyclovir, adapromine, adefovir, alafenamide, amantadine, asunaprevir, baloxavir marboxil, beclabuvir, boceprevir, brivudine, cidofovir, ciluprevir, clevudine, cytarabine, daclatasvir, danoprevir, dasabuvir, deleobuvir, dipivoxil, edoxudine, elbasvir, entecavir, faldaprevir, famciclovir, favipiravir, filibuvir, fomivirsen, foscarnet, galidesivir, ganciclovir, glecaprevir, GLS4, grazoprevir, idoxuridine, imiquimod, IFN-α, interferon alfa 2b, JNJ-440, JNJ-6379, lamivudine, laninamivir, ledipasvir, mericitabine, methisazone, MK-608, moroxydine, narlaprevir, NITD008, NZ-4, odalasvir, ombitasvir, oseltamivir, paritaprevir, peginterferon alfa-2a, penciclovir, peramivir, pibrentasvir, pimodivir, pleconaril, podophyllotoxin, presatovir, radalbuvir, ravidasvir, remdesivir, REP 2139, REP 2165, resiquimod, RG7907, ribavirin, rifampicin, rimantadine, ruzasvir, samatasvir, setrobuvir, simeprevir, sofosbuvir, sorivudine, sovaprevir, taribavirin, telaprevir, telbivudine, tenofovir, tenofovir disoproxil, triazavirin, trifluridine, tromantadine, umifenovir, uprifosbuvir, valaciclovir, valgancicovir, vaniprevir, vedroprevir, velpatasvir, vidarabine, voxilaprevir, or zanamivir, or any combination thereof.

The term "% w/w" or "% wt/wt" as used herein has its ordinary meaning as understood in light of the specification and refers to a percentage expressed in terms of the weight of the ingredient or agent over the total weight of the composition multiplied by 100. The term "% v/v" or "% vol/vol" as used herein has its ordinary meaning as understood in the light of the specification and refers to a percentage expressed in terms of the liquid volume of the compound, substance, ingredient, or agent over the total liquid volume of the composition multiplied by 100.

The invention is generally disclosed herein using affirmative language to describe the numerous embodiments. The invention also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1: siRNA Design siRNAs of 18-21 nucleotides in length were selected. Mismatches were allowed only outside of the seed region on the antisense strand, as shown in Table 7. The seed region is in positions 2-8, with the position numbering based on the antisense strand. The strand length excludes the two nucleotide overhang.

TABLE 7

Allowed mismatch positions in siRNAs

| siRNA length | Maximum mismatches | Fully conserved positions (seed region) | Allowed mismatch positions |
|---|---|---|---|
| 18 | 2 | 2-8 | 1, 9, 10, 11, 12, 13, 14, 15, 16, 17, 18 |
| 19 | 2 | 2-8 | 1, 9, 10, 11, 12, 13, 14, 15, 16, 17, 18, 19 |
| 20 | 2 | 2-8 | 1, 9, 10, 11, 12, 13, 14, 15, 16, 17, 18, 19, 20 |
| 21 | 2 | 2-8 | 1, 9, 10, 11, 12, 13, 14, 15, 16, 17, 18, 19, 20, 21 |

Example 2: siRNAs Targeting the Human CD274 Gene (PD-L1)

siRNAs were designed using the human CD274 mRNA transcript (NCBI accession number NM_014143.4, 3634 nt in length, SEQ ID NO: 1) as the template. 18-mers are listed in Table 8 (SEQ ID NOs: 2-93). 19-mers are depicted in Table 9 (SEQ ID NOs: 94-167 and 283-380). 20-mers are depicted in Table 10 (SEQ ID NOs: 168-229). 21-mers are depicted in Table 11 (SEQ ID NOs: 230-282). All of the listed siRNAs depict the antisense strand. Sense strands (which are not listed) are perfectly complementary to each listed antisense strand.

Any of the siRNAs listed herein, and the individual nucleobases, sugars, linkages, nucleosides, nucleotides and additional moieties thereof, can be constructed and used with any of the modifications described herein. The sequences listed in Tables 8-11 and SEQ ID NOs: 2-380 represent the unmodified oligonucleotide sequence prior to application of modifications.

TABLE 8

CD274 siRNAs - 18-mers

| Target start position | Target positions spanned | siRNA Antisense Strand Sequence | SEQ ID NO: |
|---|---|---|---|
| 69 | 86-69 | ACAGCAAATATCCTCATC | 2 |
| 70 | 87-70 | GACAGCAAATATCCTCAT | 3 |
| 71 | 88-71 | AGACAGCAAATATCCTCA | 4 |
| 72 | 89-72 | AAGACAGCAAATATCCTC | 5 |
| 73 | 90-73 | AAAGACAGCAAATATCCT | 6 |
| 74 | 91-74 | TAAAGACAGCAAATATCC | 7 |
| 75 | 92-75 | ATAAAGACAGCAAATATC | 8 |
| 76 | 93-76 | TATAAAGACAGCAAATAT | 9 |
| 77 | 94-77 | ATATAAAGACAGCAAATA | 10 |
| 78 | 95-78 | AATATAAAGACAGCAAAT | 11 |
| 1398 | 1415-1398 | AGACTCAAAATAAATAGG | 12 |
| 1399 | 1416-1399 | CAGACTCAAAATAAATAG | 13 |
| 1400 | 1417-1400 | ACAGACTCAAAATAAATA | 14 |
| 1401 | 1418-1401 | CACAGACTCAAAATAAAT | 15 |
| 1402 | 1419-1402 | TCACAGACTCAAAATAAA | 16 |
| 1403 | 1420-1403 | CTCACAGACTCAAAATAA | 17 |
| 1404 | 1421-1404 | CCTCACAGACTCAAAATA | 18 |
| 1405 | 1422-1405 | ACCTCACAGACTCAAAAT | 19 |
| 1406 | 1423-1406 | GACCTCACAGACTCAAAA | 20 |
| 1407 | 1424-1407 | AGACCTCACAGACTCAAA | 21 |
| 2700 | 2717-2700 | ATAACTTAGAAACAAAGA | 22 |
| 2701 | 2718-2701 | GATAACTTAGAAACAAAG | 23 |

TABLE 8-continued

CD274 siRNAs - 18-mers

| Target start position | Target positions spanned | siRNA Antisense Strand Sequence | SEQ ID NO: |
|---|---|---|---|
| 2702 | 2719-2702 | AGATAACTTAGAAACAAA | 24 |
| 277 | 294-277 | CTTCAGGTCTTCCTCTCC | 25 |
| 3038 | 3055-3038 | GGTAGCTAGCAGTCAAGG | 26 |
| 3039 | 3056-3039 | GGGTAGCTAGCAGTCAAG | 27 |
| 3040 | 3057-3040 | AGGGTAGCTAGCAGTCAA | 28 |
| 3041 | 3058-3041 | CAGGGTAGCTAGCAGTCA | 29 |
| 3239 | 3256-3239 | TTCAGCCTTGACATGTGG | 30 |
| 3240 | 3257-3240 | CTTCAGCCTTGACATGTG | 31 |
| 3241 | 3258-3241 | TCTTCAGCCTTGACATGT | 32 |
| 3242 | 3259-3242 | TTCTTCAGCCTTGACATG | 33 |
| 3243 | 3260-3243 | TTTCTTCAGCCTTGACAT | 34 |
| 350 | 367-350 | GAAGTGCAGCATTTCCCA | 35 |
| 351 | 368-351 | TGAAGTGCAGCATTTCCC | 36 |
| 352 | 369-352 | CTGAAGTGCAGCATTTCC | 37 |
| 3527 | 3544-3527 | TTTATTAAATTAATGCAG | 38 |
| 3528 | 3545-3528 | TTTTATTAAATTAATGCA | 39 |
| 3529 | 3546-3529 | ATTTTATTAAATTAATGC | 40 |
| 353 | 370-353 | TCTGAAGTGCAGCATTTC | 41 |
| 354 | 371-354 | ATCTGAAGTGCAGCATTT | 42 |
| 3542 | 3559-3542 | AATAAATAAGAATATTTT | 43 |
| 355 | 372-355 | GATCTGAAGTGCAGCATT | 44 |
| 363 | 380-363 | ACATCTGTGATCTGAAGT | 45 |
| 364 | 381-364 | CACATCTGTGATCTGAAG | 46 |
| 365 | 382-365 | TCACATCTGTGATCTGAA | 47 |
| 366 | 383-366 | TTCACATCTGTGATCTGA | 48 |
| 414 | 431-414 | GCACCACCATAGCTGATC | 49 |
| 415 | 432-415 | GGCACCACCATAGCTGAT | 50 |
| 423 | 440-423 | TTGTAGTCGGCACCACCA | 51 |
| 424 | 441-424 | CTTGTAGTCGGCACCACC | 52 |
| 432 | 449-432 | GTAATTCGCTTGTAGTCG | 53 |
| 433 | 450-433 | AGTAATTCGCTTGTAGTC | 54 |
| 451 | 468-451 | TGGGGCATTGACTTTCAC | 55 |
| 452 | 469-452 | ATGGGGCATTGACTTTCA | 56 |
| 453 | 470-453 | TATGGGGCATTGACTTTC | 57 |
| 454 | 471-454 | GTATGGGGCATTGACTTT | 58 |
| 455 | 472-455 | TGTATGGGGCATTGACTT | 59 |
| 456 | 473-456 | TTGTATGGGGCATTGACT | 60 |
| 457 | 474-457 | GTTGTATGGGGCATTGAC | 61 |
| 458 | 475-458 | TGTTGTATGGGGCATTGA | 62 |
| 459 | 476-459 | TTGTTGTATGGGGCATTG | 63 |
| 460 | 477-460 | TTTGTTGTATGGGGCATT | 64 |
| 461 | 478-461 | TTTTGTTGTATGGGGCAT | 65 |
| 462 | 479-462 | ATTTTGTTGTATGGGGCA | 66 |
| 463 | 480-463 | GATTTTGTTGTATGGGGC | 67 |
| 464 | 481-464 | TGATTTTGTTGTATGGGG | 68 |
| 473 | 490-473 | TTCTTTGGTTGATTTTGT | 69 |
| 474 | 491-474 | ATTCTTTGGTTGATTTTG | 70 |
| 475 | 492-475 | AATTCTTTGGTTGATTTT | 71 |
| 476 | 493-476 | AAATTCTTTGGTTGATTT | 72 |
| 477 | 494-477 | AAAATTCTTTGGTTGATT | 73 |
| 499 | 516-499 | AGAGGTGACTGGATCCAC | 74 |
| 500 | 517-500 | CAGAGGTGACTGGATCCA | 75 |
| 501 | 518-501 | TCAGAGGTGACTGGATCC | 76 |
| 520 | 537-520 | CTGACATGTCAGTTCATG | 77 |
| 531 | 548-531 | TAGCCCTCAGCCTGACAT | 78 |
| 564 | 581-564 | TCACTGCTTGTCCAGATG | 79 |
| 565 | 582-565 | GTCACTGCTTGTCCAGAT | 80 |
| 566 | 583-566 | GGTCACTGCTTGTCCAGA | 81 |
| 567 | 584-567 | TGGTCACTGCTTGTCCAG | 82 |
| 641 | 658-641 | GTGTGCTGGTCACATTGA | 83 |
| 642 | 659-642 | AGTGTGCTGGTCACATTG | 84 |
| 643 | 660-643 | CAGTGTGCTGGTCACATT | 85 |
| 644 | 661-644 | TCAGTGTGCTGGTCACAT | 86 |
| 645 | 662-645 | CTCAGTGTGCTGGTCACA | 87 |
| 742 | 759-742 | AGGTAGTTCTGGGATGAC | 88 |
| 743 | 760-743 | GAGGTAGTTCTGGGATGA | 89 |
| 893 | 910-893 | TCTTTGAGTTTGTATCTT | 90 |
| 894 | 911-894 | TTCTTTGAGTTTGTATCT | 91 |
| 918 | 935-918 | TCCTCCAAATGTGTATCA | 92 |
| 919 | 936-919 | CTCCTCCAAATGTGTATC | 93 |

TABLE 9

CD274 siRNAs - 19 mers

| Target start position | Target positions spanned | siRNA Antisense Strand Sequence | SEQ ID NO: |
|---|---|---|---|
| 69 | 87-69 | GACAGCAAATATCCTCATC | 94 |
| 70 | 88-70 | AGACAGCAAATATCCTCAT | 95 |
| 71 | 89-71 | AAGACAGCAAATATCCTCA | 96 |
| 72 | 90-72 | AAAGACAGCAAATATCCTC | 97 |
| 73 | 91-73 | TAAAGACAGCAAATATCCT | 98 |
| 74 | 92-74 | ATAAAGACAGCAAATATCC | 99 |
| 75 | 93-75 | TATAAAGACAGCAAATATC | 100 |
| 76 | 94-76 | ATATAAAGACAGCAAATAT | 101 |
| 77 | 95-77 | AATATAAAGACAGCAAATA | 102 |
| 78 | 96-78 | GAATATAAAGACAGCAAAT | 103 |
| 1398 | 1416-1398 | CAGACTCAAAATAAATAGG | 104 |
| 1399 | 1417-1399 | ACAGACTCAAAATAAATAG | 105 |
| 1400 | 1418-1400 | CACAGACTCAAAATAAATA | 106 |
| 1401 | 1419-1401 | TCACAGACTCAAAATAAAT | 107 |
| 1402 | 1420-1402 | CTCACAGACTCAAAATAAA | 108 |
| 1403 | 1421-1403 | CCTCACAGACTCAAAATAA | 109 |
| 1404 | 1422-1404 | ACCTCACAGACTCAAAATA | 110 |
| 1405 | 1423-1405 | GACCTCACAGACTCAAAAT | 111 |
| 1406 | 1424-1406 | AGACCTCACAGACTCAAAA | 112 |
| 2700 | 2718-2700 | GATAACTTAGAAACAAAGA | 113 |
| 2701 | 2719-2701 | AGATAACTTAGAAACAAAG | 114 |
| 3038 | 3056-3038 | GGGTAGCTAGCAGTCAAGG | 115 |
| 3039 | 3057-3039 | AGGGTAGCTAGCAGTCAAG | 116 |
| 3040 | 3058-3040 | CAGGGTAGCTAGCAGTCAA | 117 |
| 3239 | 3257-3239 | CTTCAGCCTTGACATGTGG | 118 |
| 3240 | 3258-3240 | TCTTCAGCCTTGACATGTG | 119 |
| 3241 | 3259-3241 | TTCTTCAGCCTTGACATGT | 120 |
| 3242 | 3260-3242 | TTTCTTCAGCCTTGACATG | 121 |
| 3243 | 3261-3243 | GTTTCTTCAGCCTTGACAT | 122 |
| 350 | 368-350 | TGAAGTGCAGCATTTCCCA | 123 |
| 351 | 369-351 | CTGAAGTGCAGCATTTCCC | 124 |
| 352 | 370-352 | TCTGAAGTGCAGCATTTCC | 125 |
| 3527 | 3545-3527 | TTTTATTAAATTAATGCAG | 126 |
| 3528 | 3546-3528 | ATTTTATTAAATTAATGCA | 127 |
| 353 | 371-353 | ATCTGAAGTGCAGCATTTC | 128 |
| 354 | 372-354 | GATCTGAAGTGCAGCATTT | 129 |
| 355 | 373-355 | TGATCTGAAGTGCAGCATT | 130 |
| 364 | 382-364 | TCACATCTGTGATCTGAAG | 131 |
| 365 | 383-365 | TTCACATCTGTGATCTGAA | 132 |
| 415 | 433-415 | CGGCACCACCATAGCTGAT | 133 |
| 423 | 441-423 | CTTGTAGTCGGCACCACCA | 134 |
| 424 | 442-424 | GCTTGTAGTCGGCACCACC | 135 |
| 451 | 469-451 | ATGGGGCATTGACTTTCAC | 136 |
| 452 | 470-452 | TATGGGGCATTGACTTTCA | 137 |
| 453 | 471-453 | GTATGGGGCATTGACTTTC | 138 |
| 454 | 472-454 | TGTATGGGGCATTGACTTT | 139 |
| 455 | 473-455 | TTGTATGGGGCATTGACTT | 140 |
| 456 | 474-456 | GTTGTATGGGGCATTGACT | 141 |
| 457 | 475-457 | TGTTGTATGGGGCATTGAC | 142 |
| 458 | 476-458 | TTGTTGTATGGGGCATTGA | 143 |
| 459 | 477-459 | TTTGTTGTATGGGGCATTG | 144 |
| 460 | 478-460 | TTTTGTTGTATGGGGCATT | 145 |
| 461 | 479-461 | ATTTTGTTGTATGGGGCAT | 146 |
| 462 | 480-462 | GATTTTGTTGTATGGGGCA | 147 |
| 463 | 481-463 | TGATTTTGTTGTATGGGGC | 148 |
| 464 | 482-464 | TTGATTTTGTTGTATGGGG | 149 |
| 473 | 491-473 | ATTCTTTGGTTGATTTTGT | 150 |
| 474 | 492-474 | AATTCTTTGGTTGATTTTG | 151 |
| 475 | 493-475 | AAATTCTTTGGTTGATTTT | 152 |
| 476 | 494-476 | AAAATTCTTTGGTTGATTT | 153 |
| 499 | 517-499 | CAGAGGTGACTGGATCCAC | 154 |
| 500 | 518-500 | TCAGAGGTGACTGGATCCA | 155 |
| 520 | 538-520 | CCTGACATGTCAGTTCATG | 156 |
| 564 | 582-564 | GTCACTGCTTGTCCAGATG | 157 |
| 565 | 583-565 | GGTCACTGCTTGTCCAGAT | 158 |
| 566 | 584-566 | TGGTCACTGCTTGTCCAGA | 159 |
| 567 | 585-567 | ATGGTCACTGCTTGTCCAG | 160 |
| 641 | 659-641 | AGTGTGCTGGTCACATTGA | 161 |
| 642 | 660-642 | CAGTGTGCTGGTCACATTG | 162 |
| 643 | 661-643 | TCAGTGTGCTGGTCACATT | 163 |
| 644 | 662-644 | CTCAGTGTGCTGGTCACAT | 164 |
| 893 | 911-893 | TTCTTTGAGTTTGTATCTT | 165 |
| 918 | 936-918 | CTCCTCCAAATGTGTATCA | 166 |
| 919 | 937-919 | TCTCCTCCAAATGTGTATC | 167 |

TABLE 9-continued

CD274 siRNAs - 19 mers

| Target start position | Target positions spanned | siRNA Antisense Strand Sequence | SEQ ID NO: |
|---|---|---|---|
| 23 | 41-23 | AAGCGCGGCTGGTGCGGAG | 283 |
| 43 | 61-43 | AATGCCCTGCAGGCGGACA | 284 |
| 103 | 121-103 | CGTTCAGCAAATGCCAGTA | 285 |
| 123 | 141-123 | GGGAACCGTGACAGTAAAT | 286 |
| 143 | 161-143 | TCTACCACATATAGGTCCT | 287 |
| 163 | 181-163 | TTGTCATATTGCTACCATA | 288 |
| 183 | 201-183 | TACTGGGAATTTGCATTCA | 289 |
| 203 | 221-203 | GCCAGGTCTAATTGTTTTT | 290 |
| 223 | 241-223 | CCCAATAGACAATTAGTGC | 291 |
| 263 | 281-263 | TCTCCATGCACAAATTGAA | 292 |
| 283 | 301-283 | GCTGAACCTTCAGGTCTTC | 293 |
| 303 | 321-303 | CCTCTGTCTGTAGCTACTA | 294 |
| 323 | 341-323 | TGGTCCTTCAACAGCCGGG | 295 |
| 543 | 561-543 | TTCGGCCTTGGGGTAGCCC | 296 |
| 603 | 621-603 | GGAATTGGTGGTGGTGTTG | 297 |
| 723 | 741-723 | CAATTCAGCTGTATGGTTT | 298 |
| 763 | 781-763 | TTTCATTTGGAGGATGTGC | 299 |
| 803 | 821-803 | AGGCATAATAAGATGGCTC | 300 |
| 823 | 841-823 | TGAATGTCAGTGCTACACC | 301 |
| 843 | 861-843 | CCCTTTTCTTAAACGGAAG | 302 |
| 863 | 881-863 | TTTTTCACATCCATCATTC | 303 |
| 963 | 981-963 | GAGAATCCCTGCTTGAAGA | 304 |
| 983 | 1001-983 | GAACCCCTAAACCACAGGT | 305 |
| 1063 | 1081-1063 | TCAGTGCTTGGGCCTTTTA | 306 |
| 1083 | 1101-1083 | GCTTTCGCCAGGTTCCATT | 307 |
| 1183 | 1201-1183 | CCCTGTCACAGGCGTCGAT | 308 |
| 1203 | 1221-1203 | TGTTCAGAAGTATCCTTTC | 309 |
| 1263 | 1281-1263 | TTAGGGATTCTCAACCCGT | 310 |
| 1283 | 1301-1283 | TGCAGGAACTGACCCTCAA | 311 |
| 1323 | 1341-1323 | AAAACAAATTGAGGCATTG | 312 |
| 1363 | 1381-1363 | ATACTGTCCCGTTCCAACA | 313 |
| 1443 | 1461-1443 | AAAAGAAATCATTCACAAC | 314 |
| 1483 | 1501-1483 | TTTGGCGACAAAATTGTAA | 315 |
| 1503 | 1521-1503 | TCATTAAGCAGCAAGTTTA | 316 |
| 1543 | 1561-1543 | CACCTTACAAATACTCCAT | 317 |
| 1583 | 1601-1583 | ATGCTTCCAATGTATACTT | 318 |
| 1603 | 1621-1603 | CAACCAACGGTTTGATCTT | 319 |
| 1623 | 1641-1623 | AATAAAGGTGACATCCTAT | 320 |
| 1683 | 1701-1683 | ACTGCACAGACACTTGAGG | 321 |
| 1703 | 1721-1703 | GATATTTAAATGGAACAGA | 322 |
| 1723 | 1741-1723 | TACCACATAATTGTAAAGC | 323 |
| 1743 | 1761-1743 | ATGAGATTATGTGTGTAGG | 324 |
| 1843 | 1861-1843 | ATTTACTGGTTTGGGCAAG | 325 |
| 1863 | 1881-1863 | GTGGCAGTCTGAGGTCTGA | 326 |
| 1883 | 1901-1883 | GTATTATAAAAGGACAGTG | 327 |
| 1903 | 1921-1903 | GTAAAATATAGCTGTAAAT | 328 |
| 1923 | 1941-1923 | GAATAAAGAAATTGCTTAA | 329 |
| 1943 | 1961-1943 | GCACTTAATAAATGGTTTT | 330 |
| 1963 | 1981-1963 | CAGCGATTGATATTGCAAG | 331 |
| 2003 | 2021-2003 | TACTTTGTCTTGCTCACAT | 332 |
| 2043 | 2061-2043 | GTTAATCTCCTCATTATAC | 333 |
| 2083 | 2101-2083 | TGCTATGACACTGGACTAA | 334 |
| 2123 | 2141-2123 | TTGGCAACACTGCTCGGGT | 335 |
| 2163 | 2181-2163 | TATCCAACCGTCCCAGACC | 336 |
| 2203 | 2221-2203 | TGTAAATGAAAATTACTCT | 337 |
| 2223 | 2241-2223 | TTTAAGTACCGACCTCTCT | 338 |
| 2263 | 2281-2263 | ATGCTAGAAAAGGAATTCC | 339 |
| 2283 | 2301-2283 | GCAAATCAGGAATAAATAT | 340 |
| 2323 | 2341-2323 | CCAGACACTATATAAACAA | 341 |
| 2343 | 2361-2343 | GACAGAACTGTTAAACAAT | 342 |
| 2383 | 2401-2383 | AAGGTATGAATTTAAAATT | 343 |
| 2423 | 2441-2423 | AACCATCTCCCATGGGATC | 344 |
| 2443 | 2461-2443 | GGATGAAGTGGAGATTTTC | 345 |
| 2463 | 2481-2463 | GGAAACTTGAATGGCTTGG | 346 |
| 2483 | 2501-2483 | GTAGCAGTTGCTTCTGGAA | 347 |
| 2503 | 2521-2503 | GAACATATGAATGAAAGGC | 348 |
| 2563 | 2581-2563 | AAAAAATTTTAAAAATACG | 349 |
| 2583 | 2601-2583 | CAATGTGTTACTATTTAGG | 350 |
| 2643 | 2661-2643 | CCATCTGCTATATAAGAAA | 351 |
| 2663 | 2681-2663 | CTGGGAACTTCAAATTCAT | 352 |
| 2723 | 2741-2723 | AGATAATGAAAAGCTATGG | 353 |
| 2743 | 2761-2743 | CATATACTGGATCATATGA | 354 |
| 2763 | 2781-2763 | TATATGTAGGACATATTTA | 355 |
| 2783 | 2801-2783 | AAATGGTGGTTGTCTAAAT | 356 |
| 2803 | 2821-2803 | TCCTAGAGCAAATACTTAA | 357 |
| 2823 | 2841-2823 | ATAAACAAATCCAAACTCT | 358 |
| 2863 | 2881-2863 | GTGCACCCTGGAGAGCCCA | 359 |
| 2883 | 2901-2883 | TTTAGGACTAGATTGACTC | 360 |
| 2903 | 2921-2903 | AGTTAATAATAAGATTGCT | 361 |
| 2923 | 2941-2923 | GACATGATTCTGTCATACA | 362 |
| 2943 | 2961-2943 | AGCAGAAAACAAAAGTTCC | 363 |
| 2983 | 3001-2983 | TGCAAGTACAGCATCAAAG | 364 |
| 3003 | 3021-3003 | CCAGAAAGAAAATGTGATT | 365 |
| 3063 | 3081-3063 | CAACGAATGAGGCTTTTCT | 366 |
| 3083 | 3101-3083 | GGCATTCAAGGGTTCAAGC | 367 |
| 3103 | 3121-3103 | GTGTAGTGATGACAGCTGG | 368 |
| 3183 | 3201-3183 | TGGCCAAGAGGGAAAGGAA | 369 |
| 3203 | 3221-3203 | TTGTCATTGACACCAGAAT | 370 |
| 3263 | 3281-3263 | GGAGCTCTGTTGGAGACAC | 371 |
| 3283 | 3301-3283 | TGTACAAACAGATAACACA | 372 |
| 3323 | 3341-3323 | ACAAAGAACACTGTCACAC | 373 |
| 3343 | 3361-3343 | AATTCTTGCCTGTAATTCA | 374 |
| 3383 | 3401-3383 | TAGGAATAGACTGAGTAGA | 375 |
| 3423 | 3441-3423 | GTGCCTTACAAATCCAACA | 376 |
| 3443 | 3461-3443 | CATGAGACAAAAGGGATAA | 377 |
| 3463 | 3481-3463 | CTATGCCATTTACGATGAA | 378 |
| 3563 | 3581-3563 | ATGCTGGTGTACCAAGTAA | 379 |
| 3603 | 3621-3603 | TGAACATTTTATTAAACAC | 380 |

TABLE 10

CD274 siRNAs - 20 mers

| Target start position | Target positions spanned | siRNA Antisense Strand Sequence | SEQ ID NO: |
|---|---|---|---|
| 70 | 89-70 | AAGACAGCAAATATCCTCAT | 168 |
| 71 | 90-71 | AAAGACAGCAAATATCCTCA | 169 |
| 72 | 91-72 | TAAAGACAGCAAATATCCTC | 170 |
| 73 | 92-73 | ATAAAGACAGCAAATATCCT | 171 |
| 74 | 93-74 | TATAAAGACAGCAAATATCC | 172 |
| 75 | 94-75 | ATATAAAGACAGCAAATATC | 173 |
| 76 | 95-76 | AATATAAAGACAGCAAATAT | 174 |
| 77 | 96-77 | GAATATAAAGACAGCAAATA | 175 |
| 78 | 97-78 | TGAATATAAAGACAGCAAAT | 176 |
| 1398 | 1417-1398 | ACAGACTCAAAATAAATAGG | 177 |
| 1399 | 1418-1399 | CACAGACTCAAAATAAATAG | 178 |
| 1400 | 1419-1400 | TCACAGACTCAAAATAAATA | 179 |
| 1401 | 1420-1401 | CTCACAGACTCAAAATAAAT | 180 |
| 1402 | 1421-1402 | CCTCACAGACTCAAAATAAA | 181 |
| 1403 | 1422-1403 | ACCTCACAGACTCAAAATAA | 182 |
| 1404 | 1423-1404 | GACCTCACAGACTCAAAATA | 183 |
| 1405 | 1424-1405 | AGACCTCACAGACTCAAAAT | 184 |
| 2700 | 2719-2700 | AGATAACTTAGAAACAAAGA | 185 |
| 3038 | 3057-3038 | AGGGTAGCTAGCAGTCAAGG | 186 |
| 3039 | 3058-3039 | CAGGGTAGCTAGCAGTCAAG | 187 |
| 3240 | 3259-3240 | TTCTTCAGCCTTGACATGTG | 188 |
| 3241 | 3260-3241 | TTTCTTCAGCCTTGACATGT | 189 |
| 3242 | 3261-3242 | GTTTCTTCAGCCTTGACATG | 190 |
| 3243 | 3262-3243 | TGTTTCTTCAGCCTTGACAT | 191 |
| 350 | 369-350 | CTGAAGTGCAGCATTTCCCA | 192 |
| 351 | 370-351 | TCTGAAGTGCAGCATTTCCC | 193 |
| 352 | 371-352 | ATCTGAAGTGCAGCATTTCC | 194 |
| 353 | 372-353 | GATCTGAAGTGCAGCATTTC | 195 |
| 354 | 373-354 | TGATCTGAAGTGCAGCATTT | 196 |
| 355 | 374-355 | GTGATCTGAAGTGCAGCATT | 197 |
| 364 | 383-364 | TTCACATCTGTGATCTGAAG | 198 |
| 415 | 434-415 | TCGGCACCACCATAGCTGAT | 199 |
| 423 | 442-423 | GCTTGTAGTCGGCACCACCA | 200 |
| 424 | 443-424 | CGCTTGTAGTCGGCACCACC | 201 |
| 451 | 470-451 | TATGGGGCATTGACTTTCAC | 202 |
| 452 | 471-452 | GTATGGGGCATTGACTTTCA | 203 |
| 453 | 472-453 | TGTATGGGGCATTGACTTTC | 204 |
| 454 | 473-454 | TTGTATGGGGCATTGACTTT | 205 |

TABLE 10-continued

CD274 siRNAs - 20 mers

| Target start position | Target positions spanned | siRNA Antisense Strand Sequence | SEQ ID NO: |
|---|---|---|---|
| 455 | 474-455 | GTTGTATGGGGCATTGACTT | 206 |
| 456 | 475-456 | TGTTGTATGGGGCATTGACT | 207 |
| 457 | 476-457 | TTGTTGTATGGGGCATTGAC | 208 |
| 458 | 477-458 | TTTGTTGTATGGGGCATTGA | 209 |
| 459 | 478-459 | TTTTGTTGTATGGGGCATTG | 210 |
| 460 | 479-460 | ATTTTGTTGTATGGGGCATT | 211 |
| 461 | 480-461 | GATTTTGTTGTATGGGGCAT | 212 |
| 462 | 481-462 | TGATTTTGTTGTATGGGGCA | 213 |
| 463 | 482-463 | TTGATTTTGTTGTATGGGGC | 214 |
| 464 | 483-464 | GTTGATTTTGTTGTATGGGG | 215 |
| 473 | 492-473 | AATTCTTTGGTTGATTTTGT | 216 |
| 474 | 493-474 | AAATTCTTTGGTTGATTTTG | 217 |
| 475 | 494-475 | AAAATTCTTTGGTTGATTTT | 218 |
| 499 | 518-499 | TCAGAGGTGACTGGATCCAC | 219 |
| 520 | 539-520 | GCCTGACATGTCAGTTCATG | 220 |
| 564 | 583-564 | GGTCACTGCTTGTCCAGATG | 221 |
| 565 | 584-565 | TGGTCACTGCTTGTCCAGAT | 222 |
| 566 | 585-566 | ATGGTCACTGCTTGTCCAGA | 223 |
| 567 | 586-567 | GATGGTCACTGCTTGTCCAG | 224 |
| 641 | 660-641 | CAGTGTGCTGGTCACATTGA | 225 |
| 642 | 661-642 | TCAGTGTGCTGGTCACATTG | 226 |
| 643 | 662-643 | CTCAGTGTGCTGGTCACATT | 227 |
| 918 | 937-918 | TCTCCTCCAAATGTGTATCA | 228 |
| 919 | 938-919 | GTCTCCTCCAAATGTGTATC | 229 |

TABLE 11

CD274 siRNAs - 21 mers

| Target start position | Target positions spanned | siRNA Antisense Strand Sequence | SEQ ID NO: |
|---|---|---|---|
| 70 | 90-70 | AAAGACAGCAAATATCCTCAT | 230 |
| 71 | 91-71 | TAAAGACAGCAAATATCCTCA | 231 |
| 72 | 92-72 | ATAAAGACAGCAAATATCCTC | 232 |
| 73 | 93-73 | TATAAAGACAGCAAATATCCT | 233 |
| 74 | 94-74 | ATATAAAGACAGCAAATATCC | 234 |
| 75 | 95-75 | AATATAAAGACAGCAAATATC | 235 |
| 76 | 96-76 | GAATATAAAGACAGCAAATAT | 236 |
| 77 | 97-77 | TGAATATAAAGACAGCAAATA | 237 |
| 1398 | 1418-1398 | CACAGACTCAAAATAAATAGG | 238 |
| 1399 | 1419-1399 | TCACAGACTCAAAATAAATAG | 239 |
| 1400 | 1420-1400 | CTCACAGACTCAAAATAAATA | 240 |
| 1401 | 1421-1401 | CCTCACAGACTCAAAATAAAT | 241 |
| 1402 | 1422-1402 | ACCTCACAGACTCAAAATAAA | 242 |
| 1403 | 1423-1403 | GACCTCACAGACTCAAAATAA | 243 |
| 1404 | 1424-1404 | AGACCTCACAGACTCAAAATA | 244 |
| 3038 | 3058-3038 | CAGGGTAGCTAGCAGTCAAGG | 245 |
| 3240 | 3260-3240 | TTTCTTCAGCCTTGACATGTG | 246 |
| 3241 | 3261-3241 | GTTTCTTCAGCCTTGACATGT | 247 |
| 3242 | 3262-3242 | TGTTTCTTCAGCCTTGACATG | 248 |
| 3243 | 3263-3243 | CTGTTTCTTCAGCCTTGACAT | 249 |
| 350 | 370-350 | TCTGAAGTGCAGCATTTCCCA | 250 |
| 351 | 371-351 | ATCTGAAGTGCAGCATTTCCC | 251 |
| 352 | 372-352 | GATCTGAAGTGCAGCATTTCC | 252 |
| 353 | 373-353 | TGATCTGAAGTGCAGCATTTC | 253 |
| 354 | 374-354 | GTGATCTGAAGTGCAGCATTT | 254 |
| 355 | 375-355 | TGTGATCTGAAGTGCAGCATT | 255 |
| 415 | 435-415 | GTCGGCACCACCATAGCTGAT | 256 |
| 423 | 443-423 | CGCTTGTAGTCGGCACCACCA | 257 |
| 424 | 444-424 | TCGCTTGTAGTCGGCACCACC | 258 |
| 451 | 471-451 | GTATGGGGCATTGACTTTCAC | 259 |
| 452 | 472-452 | TGTATGGGGCATTGACTTTCA | 260 |
| 453 | 473-453 | TTGTATGGGGCATTGACTTTC | 261 |
| 454 | 474-454 | GTTGTATGGGGCATTGACTTT | 262 |
| 455 | 475-455 | TGTTGTATGGGGCATTGACTT | 263 |
| 456 | 476-456 | TTGTTGTATGGGGCATTGACT | 264 |
| 457 | 477-457 | TTTGTTGTATGGGGCATTGAC | 265 |
| 458 | 478-458 | TTTTGTTGTATGGGGCATTGA | 266 |
| 459 | 479-459 | ATTTTGTTGTATGGGGCATTG | 267 |
| 460 | 480-460 | GATTTTGTTGTATGGGGCATT | 268 |
| 461 | 481-461 | TGATTTTGTTGTATGGGGCAT | 269 |
| 462 | 482-462 | TTGATTTTGTTGTATGGGGCA | 270 |
| 463 | 483-463 | GTTGATTTTGTTGTATGGGGC | 271 |
| 464 | 484-464 | GGTTGATTTTGTTGTATGGGG | 272 |
| 473 | 493-473 | AAATTCTTTGGTTGATTTTGT | 273 |
| 474 | 494-474 | AAAATTCTTTGGTTGATTTTG | 274 |
| 564 | 584-564 | TGGTCACTGCTTGTCCAGATG | 275 |
| 565 | 585-565 | ATGGTCACTGCTTGTCCAGAT | 276 |
| 566 | 586-566 | GATGGTCACTGCTTGTCCAGA | 277 |
| 567 | 587-567 | TGATGGTCACTGCTTGTCCAG | 278 |
| 641 | 661-641 | TCAGTGTGCTGGTCACATTGA | 279 |
| 642 | 662-642 | CTCAGTGTGCTGGTCACATTG | 280 |
| 918 | 938-918 | GTCTCCTCCAAATGTGTATCA | 281 |
| 919 | 939-919 | CGTCTCCTCCAAATGTGTATC | 282 |

Example 3: Treatment of Cancer Using CD274 siRNAs

A human patient presents with a cancer, such as a hepatocellular carcinoma (HCC). The cancer is a non-metastatic or metastatic cancer. In the case of HCC, the patient may also have another liver condition, such as fibrosis, cirrhosis, non-alcoholic liver disease, hepatitis, hepatitis B, or hepatitis C. An effective amount of a CD274 siRNA or a pharmaceutical composition comprising an effective amount of a CD274 siRNA is administered to the patient parenterally. The CD274 siRNA is selected from the group consisting of SEQ ID NOs: 2-380, including any allowed mismatches as described herein. The CD274 siRNA can optionally have any of the modifications to individual nucleobases, sugars, linkages, nucleosides, or nucleotides as described herein. The CD274 siRNA can also optionally have a covalently conjugated targeting moiety to improve selectivity to tumor and/or liver tissue. The CD274 siRNA can be constructed of deoxyribose sugars (DNA nucleotides), ribose sugars (RNA nucleotides) or any combination thereof. The CD274 siRNA can be constructed of unmodified nucleotides or modified nucleotides or any combination thereof. The CD274 siRNA or pharmaceutical composition comprising the CD274 siRNA can optionally be administered as a combination therapy with another anti-neoplastic compound or therapy.

Following administration of an effective amount of the CD274 siRNA or the pharmaceutical composition comprising an effective amount of the CD274 siRNA, the cancer is reduced or eliminated.

Example 4: Treatment of Hepatitis B Using CD274 siRNAs

A human patient presents with a hepatitis B infection. The hepatitis B infection is acute or chronic. The hepatitis B infection may also be coincidental with a hepatitis D infection. The patient may also have another liver conditions, such as fibrosis, cirrhosis, non-alcoholic liver disease, or HCC. An effective amount of a CD274 siRNA or a pharmaceutical composition comprising an effective amount of a CD274 siRNA is administered to the patient parenterally. The CD274 siRNA is selected from the group consisting of SEQ ID NOs: 2-380. The CD274 siRNA can optionally have any of the modifications to individual nucleobases, sugars, linkages, nucleosides, or nucleotides as described herein. The CD274 siRNA can also optionally have a covalently conjugated targeting moiety to improve selectivity to liver tissue. The CD274 siRNA can be constructed of deoxyribose sugars (DNA nucleotides), ribose sugars (RNA nucleotides) or any combination thereof. The CD274 siRNA can be constructed of unmodified nucleotides or modified nucleotides or any combination thereof. The CD274 siRNA or pharmaceutical composition comprising the CD274 siRNA can optionally be administered as a combination therapy with another antiviral medication.

Following administration of an effective amount of the CD274 siRNA or the pharmaceutical composition comprising an effective amount of the CD274 siRNA, the hepatitis B infection (and optionally, hepatitis D infection) is reduced or eliminated.

Example 5: Treatment of Hepatocellular Carcinoma Cells Using siRNAs

Human hepatocellular carcinoma cells (SNU-387) were seeded at 30,000 cells/well in a 96-well plate. The siRNAs, including any of SEQ ID NOs: 2-380, were transfected with Lipofectamine RNAiMax (Life Technologies) in the seeded SNU-387 cells. The siRNAs included any of the modifications described herein, including modification of individual nucleobases, sugars, linkages, nucleosides, or nucleotides. The modifications of the siRNAs varied across different sequences. For example, in some sequences, such as SEQ ID NOs: 94-167 (19-mers), the sense strand included purines as 2'OMe and pyrimidines as 2'F, with two nucleotide overhang at the 3'-end, which are two mU nucleotides. All linkages in the modified SEQ ID NOs: 94-167 sense strand included phosphodiester (PO) linkages, except for the two most 5'- and 3'-end linkages, which were phosphorothioate (PS), for a total of four PS linkages. In addition, the antisense strands for SEQ ID NOs: 94-167 and 283-380 (19-mers) included alternating 2'OMe and 2'F pattern, starting with 2'OMe at the 5' end, with two nucleotide overhang at the 3'-end, which are two mU nucleotides. All linkages in the modified SEQ ID NOs: 94-167 antisense strand included PO linkages, except for the two most 5'- and 3'-end linkages, which were PS linkages, for a total of four PS linkages.

As another example, in some sequences, such as in SEQ ID NOs: 283-380 (19-mers), the sense strand included alternating 2'OMe and 2'F pattern, starting with 2'F at the 5' end, with two nucleotide overhang at the 3'-end, which are two mU nucleotides. All linkages in the modified SEQ ID NOs: 283-380 sense strand included phosphodiester (PO) linkages, except for the two most 5'- and 3'-end linkages, which were phosphorothioate (PS), for a total of four PS linkages. In addition, the antisense strands for SEQ ID NOs: 283-380 (19-mers) included alternating 2'OMe and 2'F pattern, starting with 2'OMe at the 5' end, with two nucleotide overhang at the 3'-end, which are two mU nucleotides. All linkages in the modified SEQ ID NOs: 283-380 antisense strand included PO linkages, except for the two most 5'- and 3'-end linkages, which were PS linkages, for a total of four PS linkages.

As another example, in some sequences, such as in SEQ ID NOs: 230-282 (21-mers), the sense strand included purines as 2'OMe and pyrimidines as 2'F, with all linkages as PO, except for the two most 5'-end linkages, which were PS linkages, for a total of two PS linkages. The sense strand in these 21-mer sequences did not include an overhang, but were blunt ended. The antisense strand for SEQ ID NOs: 230-282 (21-mers) included alternating 2'OMe and 2'F pattern, starting with 2'OMe at the 5'end, with a two nucleotide overhang at the 3'-end, which were two mU nucleotides. All linkages in the 21-mer antisense strands were PO linkages, except for the two most 5'- and 3'-end linkages, which were PS linkages, for a total of four PS linkages. It is to be understood that these modifications to these sequences are exemplary, and that any modifications as described herein on any siRNA sequence can be employed.

For dose response curves, a 4-fold dilution series of siRNA (top dose 50 nM; 6 concentrations tested total) was tested. At 48 hr post transfection, cells were harvested, RNA was extracted with RNeasy 96 Kits (Qiagen), and RT-qPCR is performed to assess PD-L1 gene knockdown. Cell viability (of separate plate treated the same way) was assessed at 48 h post transfection using Cell Titer Glo (Promega); protocol according to manufacturer's instructions. Data was fit with GraphPad Prism using a four parameter dose response equation. Table 12 provides representative EC50 and CC50 values for selected siRNA. FIG. 1 depicts the fraction of PD-L1 mRNA remaining.

TABLE 12

Relative Gene Expression for select siRNA sequences

| SEQ ID NO: | EC50 (nM) | CC50 (nM) |
|---|---|---|
| 106 | A | X |
| 125 | C | X |
| 134 | B | X |
| 127 | C | X |

A < 0.4 nM;
B = 0.4-0.8 nM;
C > 0.8-1.2 nM
X > 50 nM;
Y ≤ 50 nM

In a separate experiment, the siRNA were transfected with Lipofectamine RNAiMax (Life Technologies) in SNU-387 cells, seeded at 30,000 cells/well in 96-well plates. Two concentrations were tested (20 and 0.2 nM) for each siRNA. At 48 hr post transfection, cells were harvested, RNA was extracted with RNeasy 96 Kits (Qiagen), and RT-qPCR was performed to assess PD-L1 gene knockdown. Cell viability (of separate plate treated the same way) was assessed at 48 h post transfection using Cell Titer Glo (Promega); protocol according to manufacturer's instructions. Results are shown in Table 13; specific modifications of the siRNAs are indicated in the table, which are the modifications as described herein in Example 5.

TABLE 13

Percent Reduction of PD-L1 Gene with select siRNAs

| SEQ ID NO: | % Reduction of PD-L1 gene at 50 nM | % Reduction of PD-L1 gene at 1 nM | CC50 (nM) |
|---|---|---|---|
| 19-mers (modification pattern as described above in Example 5) | | | |
| 137 | D | C | X |
| 138 | D | D | X |
| 105 | D | D | X |
| 106 | C | A | X |
| 125 | B | C | X |
| 128 | C | D | X |
| 129 | D | C | X |
| 130 | D | D | X |
| 135 | C | C | X |
| 136 | D | D | X |
| 139 | D | C | X |
| 152 | C | C | X |

TABLE 13-continued

Percent Reduction of PD-L1 Gene with select siRNAs

| SEQ ID NO: | % Reduction of PD-L1 gene at 50 nM | % Reduction of PD-L1 gene at 1 nM | CC50 (nM) |
|---|---|---|---|
| 158 | D | D | X |
| 159 | D | D | X |
| 104 | C | C | X |
| 107 | C | C | X |
| 108 | D | C | X |
| 94 | C | D | X |
| 95 | C | C | X |
| 102 | D | D | X |
| 103 | B | B | X |
| 133 | A | B | X |
| 134 | A | C | X |
| 140 | B | C | X |
| 141 | C | C | X |
| 147 | C | C | X |
| 148 | D | C | X |
| 149 | C | D | X |
| 153 | C | D | X |
| 156 | D | D | X |
| 157 | D | D | X |
| 160 | D | D | X |
| 165 | D | D | X |
| 167 | D | D | X |
| 109 | D | D | X |
| 119 | D | D | X |
| 120 | D | D | X |
| 121 | D | D | X |
| 126 | B | C | X |
| 127 | B | D | X |
| 283 | D | D | X |
| 284 | D | D | X |
| 285 | C | D | X |
| 286 | C | D | X |
| 287 | D | D | X |
| 288 | C | D | X |
| 289 | D | D | X |
| 290 | D | D | X |
| 291 | C | D | X |
| 292 | C | D | X |
| 293 | D | D | X |
| 294 | D | D | X |
| 295 | D | D | X |
| 296 | D | D | X |
| 297 | C | D | X |
| 298 | C | D | X |
| 299 | C | D | X |
| 300 | B | D | X |
| 301 | B | D | X |
| 302 | D | D | X |
| 303 | B | D | X |
| 304 | D | D | X |
| 305 | B | D | X |
| 306 | D | D | X |
| 307 | B | D | X |
| 308 | D | D | X |
| 309 | B | D | X |
| 310 | C | D | X |
| 311 | D | D | X |
| 312 | B | C | X |
| 313 | C | D | X |
| 314 | B | C | X |
| 315 | C | C | X |
| 317 | C | D | X |
| 318 | B | D | X |
| 319 | C | D | X |
| 320 | B | C | X |
| 321 | B | D | X |
| 322 | B | D | X |
| 323 | C | D | X |
| 324 | B | C | X |
| 325 | C | D | X |
| 326 | D | D | X |
| 327 | C | D | X |
| 328 | C | D | X |
| 329 | C | D | X |
| 330 | D | D | X |
| 331 | B | C | X |
| 332 | C | D | X |
| 333 | C | D | X |
| 334 | D | D | X |
| 335 | C | D | X |
| 336 | B | C | X |
| 337 | B | C | X |
| 338 | D | D | X |
| 339 | B | C | X |
| 340 | C | D | X |
| 341 | D | D | X |
| 342 | B | D | X |
| 343 | B | D | X |
| 344 | D | D | X |
| 345 | D | D | X |
| 346 | C | D | X |
| 347 | D | D | X |
| 348 | C | D | X |
| 349 | D | D | X |
| 350 | C | D | X |
| 351 | D | D | X |
| 352 | B | D | X |
| 354 | D | D | X |
| 373 | B | C | X |
| 374 | C | C | X |
| 375 | C | C | X |
| 376 | C | D | X |
| 377 | C | C | X |
| 378 | C | C | X |
| 379 | D | D | X |
| 380 | C | D | X |

21-mers (modification pattern as described above in Example 5)

| SEQ ID NO: | % Reduction of PD-L1 gene at 50 nM | % Reduction of PD-L1 gene at 1 nM | CC50 (nM) |
|---|---|---|---|
| 230 | B | C | X |
| 237 | A | B | X |
| 252 | D | D | X |
| 253 | D | D | X |
| 254 | D | D | X |
| 255 | D | D | X |
| 256 | D | D | X |
| 257 | D | D | X |
| 258 | D | C | X |
| 259 | D | D | X |
| 260 | D | D | X |
| 261 | D | D | X |
| 262 | B | D | X |
| 263 | A | C | X |
| 264 | B | D | X |
| 270 | B | D | X |
| 271 | B | C | X |
| 272 | C | D | X |
| 275 | C | B | X |
| 276 | C | D | X |
| 277 | D | D | X |
| 278 | D | D | X |
| 282 | B | D | X |
| 238 | B | D | X |
| 239 | C | D | X |
| 240 | D | D | X |
| 241 | D | D | X |
| 242 | D | D | X |
| 243 | C | D | X |
| 246 | C | C | X |
| 247 | C | D | X |
| 248 | D | D | X |

A > 75%-100%;
B > 50%-75%;
C > 25%-50%;
D = 0%-25%
X > 20 nM;
Y ≤ 20 nM

Example 6: In Vivo Treatment of Mice with siRNA

Figure 2:
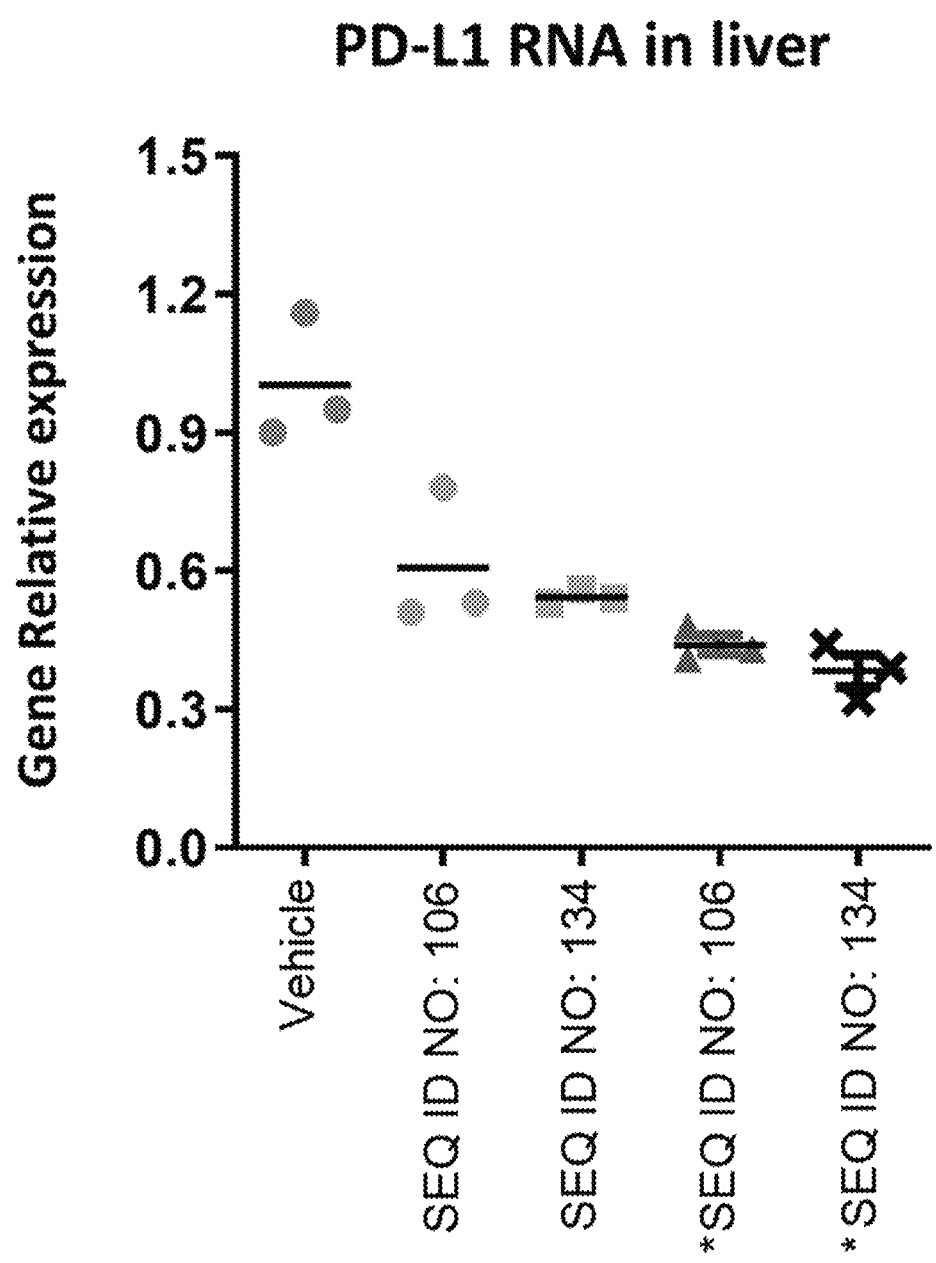
FIG. 2 depicts relative gene expression for PD-L1 RNA in mouse liver 72 hours after treatment with exemplary modified siRNA sequences provided herein.

C57BL/6 mice were provided. One subcutaneous dose of 7.5 mg/kg siRNA or vehicle (phosphate buffered saline) was administered in mice (n=4 per group) on day 0. The siRNA included any of SEQ ID NOs: 2-380, including any modification described herein. On day 3, 10 mg/kg low molecular weight polyI:C (LMW PIC, from Invivogen) was dosed by IV to all groups. Mice were sacrificed 5 hours post-LMW PIC dose. Liver was sectioned and placed in RNALater (Qiagen) for RNA extraction. RNA was extracted from liver samples and PD-L1 gene expression was measured by RT-qPCR. P values were determined from a t-test comparing treatment groups to vehicle control. The values are provided in FIG. 2, and in Table 14.

TABLE 14

Relative Gene Expression for select siRNA sequences

| SEQ ID NO: | Modification | Relative Gene Expression | P value (t-test) Compared to Vehicle Group |
|---|---|---|---|
| Vehicle | | 1.01 | |
| 106 | 3'GalNac4 on S strand | 0.61 | 0.029 |
| 134 | 3'GalNac4 on S strand | 0.54 | 0.027 |
| 106 | 5'VP on AS strand 3'GalNac4 on S strand | 0.44 | 0.002 |
| 134 | 5'VP on AS strand 3'GalNac4 on S strand | 0.38 | 0.002 |

The sequences including the modifications for each of the siRNAs as set forth in Table 14 are provided below in Table 15:

TABLE 15

Sequence modifications for sense strand and antisense strand of siRNAs of Table 14

| SEQ ID NO: | Sequence (5' to 3') |
|---|---|
| 106 | S strand: fUpsmApsfUfUfUmAfUfUfUfUmGmAm-GfUfCfUmGfUmGGalNAc4<br>AS strand: mCpsfApsmCfAmGfAmCfUmCfAmAfAmAfUmAf-AmAfUmApsmUpsmU |
| 134 | S strand: fUpsmGpsmGfUmGmGfUmGfCfCmGmAf-CfUmAfCmAmAmGGalNAc4<br>AS strand: mCpsfUpsmUfGmUfAmGfUmCfGmGfCmAfCmCf-AmCfCmApsmUpsmU |
| 106 | S strand: fUpsmApsfUfUfUmAfUfUfUfUmGmAmG-fUfCfUmGfUmGGalNAc4<br>AS strand: VPmCpsfApsmCfAmGfAmCfUmCfAmAfAmAfUm-AfAmAfUmApsmUpsmU |
| 134 | S strand: fUpsmGpsmGfUmGmGfUmGfCfCmGmAf-CfUmAfCmAmAmGGalNAc4<br>AS strand: VPmCpsfUpsmUfGmUfAmGfUmCfGmGfCmAfCmCf-AmCfCmApsmUpsmU |

The example siRNAs, including the example sequences and example modifications as described in the examples, are intended as exemplary sequences and modifications. However, it is to be understood that the disclosure relates to any siRNA sequence as set forth herein, having any modification or combination of modifications as set forth herein may be implemented in the examples.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description or claims, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

REFERENCES

1. U.S. 2017/0283496
2. Akinleye, A & Rasool Z. Immune Checkpoint Inhibitors of PD-L1 as Cancer Therapeutics. *J. Hematol. Oncol.* (2019) 12(1):92.
3. Wu, Y et al. PD-L1 Distribution and Perspective for Cancer Immunotherapy—Blockade, Knockdown, or Inhibition. *Front. Immunol.* (2019) 10:2022.
4. Sun, C et al. Regulation and Function of the PD-L1 Checkpoint. *Immunity.* (2018) 48(3):434-452.
5. Schönrich, G & Raferty M J. The PD-1/PD-L1 Axis and Virus Infections: A Delicate Balance. *Front. Cell. Infect. Microbiol.* (2019) 9:207
6. Østergaard, M E et al. Fluorinated Nucleotide Modifications Modulate Allele Selectivity of SNP-Targeting Antisense Oligonucleotides. *Mol. Ther. Nucleic Acids.* (2017) 7:20-30.
7. Di Fusco, D et al. Antisense Oligonucleotide: Basic Concepts and Therapeutic Application in Inflammatory Bowel Disease. *Front Pharmacol.* (2019) 10:305.
8. Wurster, C D & Ludolph A C. Antisense Oligonucleotides in Neurological Disorders. *Ther. Adv. Neurol. Disord.* (2018) 11:1-19.
9. Balsitis S et al. Safety and Efficacy of Anti-PD-L1 Therapy in the Woodchuck Model of HBV Infection. (2018) 13(2):1-23.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A small interfering RNA (siRNA) that targets human CD274 mRNA, comprising a sense strand and an antisense strand, wherein the antisense strand comprises nucleotides selected from the group consisting of unmodified nucleotides and modified nucleosides,
   wherein each modified nucleoside contains a modified sugar, contains a modified nucleobase or is abasic, or both contains a modified sugar and contains a modified nucleobase or is abasic;
   wherein each linkage between the nucleosides is a phosphorothioate, phosphodiester, phosphoramidate, thiophosphoramidate, methylphosphate, methylphosphonate, phosphonoacetate, amide, boranophosphate, or any combination thereof;
   wherein the siRNA has a sequence as set forth in any one of SEQ ID NO: 303, and is at least 85% complementary to a fragment of human CD274 mRNA; and
   wherein the antisense strand comprises a 5'-phosphate mimic.

2. The siRNA of claim 1, wherein the siRNA comprises zero, one, or two mismatches to the fragment of human CD274 mRNA.

3. The siRNA of claim 2, wherein the mismatches occur at any one or more of positions 1 or 9 through m, wherein m is the total number of nucleotides in the antisense strand.

4. The siRNA of claim 2, wherein the mismatches do not occur at a seed region of the siRNA.

5. The siRNA of claim 4, wherein the seed region is at positions 2-8.

6. The siRNA of claim 1, further comprising a 2-nucleotide overhang.

7. The siRNA of claim 6, wherein the 2-nucleotide overhang is non-complementary to the CD274 mRNA.

8. The siRNA of claim 1, wherein the modified sugar is selected from the group consisting of 2'-OMe, 2'-F, 2'-MOE, 2'-araF, 2'-araOH, 2'-OEt, 2'-O-alkyl, LNA, scpBNA, AmNA, cEt, ENA, and GNA.

9. The siRNA of claim 1, wherein the 5'-phosphate mimic is a 5'-vinylphosphonate.

10. The siRNA of claim 1, further comprising a targeting moiety.

11. The siRNA of claim 10, wherein the targeting moiety is conjugated to the siRNA at the 5' end, 3' end, or both.

12. The siRNA of claim 10, wherein the targeting moiety is a fatty acid, GalNAc, folic acid, cholesterol, tocopherol, or palmitate.

13. The siRNA of claim 1, wherein the modified nucleoside is selected from the group consisting of:

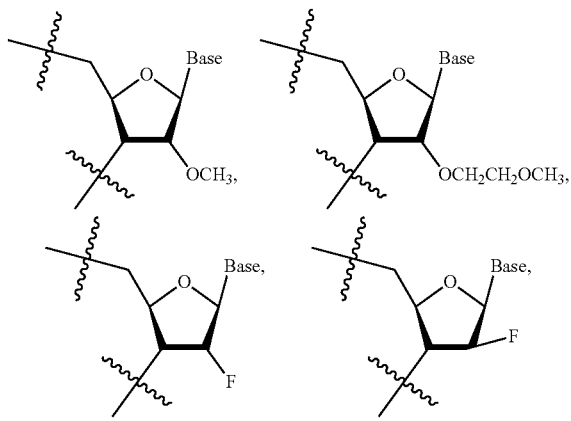

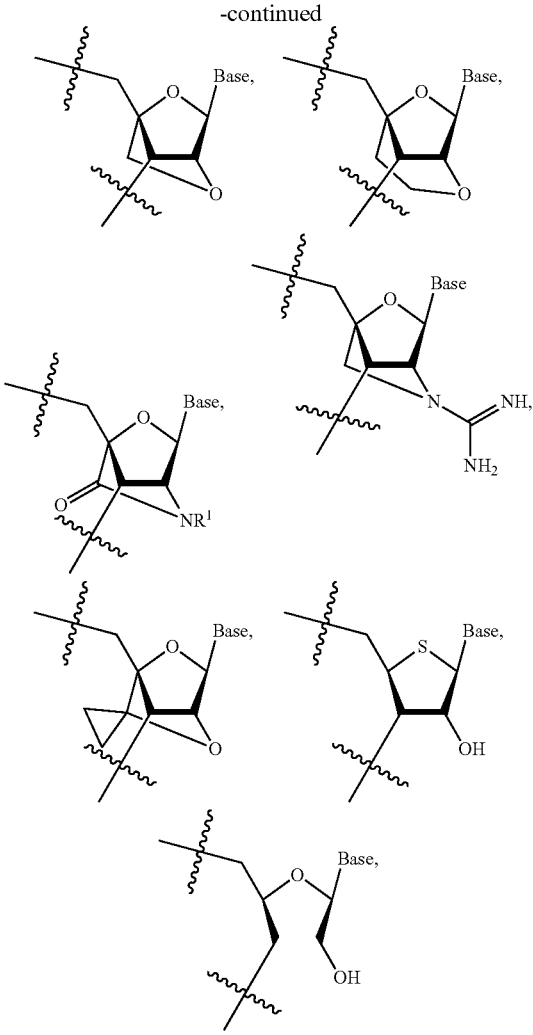

and

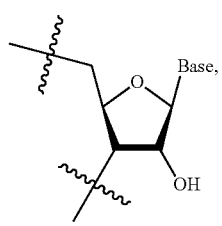

wherein $R^1$ is hydrogen or $C_{1-7}$ alkyl.

14. The siRNA of claim 13, wherein the Base is selected from the group consisting of adenine, guanine, cytosine, 5-methyl cytosine, thymine, and uracil.

15. A pharmaceutical composition comprising an effective amount of the siRNA according to claim 1 and a pharmaceutically acceptable carrier, diluent, excipient, or combination thereof.

16. A method for treating hepatitis B in a subject comprising administering to the subject in need thereof an effective amount of an siRNA of claim 1.

17. A method for treating hepatocellular carcinoma (HCC) in a subject comprising administering to the subject in need thereof an effective amount of an siRNA of claim 1.

18. The method of claim 17, further comprising administering surgery, radiation therapy, chemotherapy, targeted therapy, immunotherapy, hormonal therapy, or antiviral therapy.

* * * * *